United States Patent
Levine et al.

(10) Patent No.: US 9,574,217 B2
(45) Date of Patent: Feb. 21, 2017

(54) MULTI-STAGE PROCESS FOR PRODUCTION OF IMMUNE MODULATOR

(71) Applicant: Algal Scientific Corporation, Plymouth, MI (US)

(72) Inventors: Robert Bernard Levine, Ann Arbor, MI (US); Jeffrey Richard LeBrun, Ann Arbor, MI (US); Geoffrey Paul Horst, Grosse Pointe Farms, MI (US)

(73) Assignee: Algal Scientific Corporation, Plymouth, MI (US)

( * ) Notice: Subject to any disclaimer, the term of this patent is extended or adjusted under 35 U.S.C. 154(b) by 0 days.

(21) Appl. No.: 13/888,852

(22) Filed: May 7, 2013

(65) Prior Publication Data

US 2013/0303752 A1    Nov. 14, 2013

Related U.S. Application Data

(60) Provisional application No. 61/643,572, filed on May 7, 2012.

(51) Int. Cl.
*C12P 19/04* (2006.01)
*C08B 37/00* (2006.01)
(Continued)

(52) U.S. Cl.
CPC ............. *C12P 19/04* (2013.01); *A23L 17/60* (2016.08); *A23L 33/10* (2016.08); *C08B 37/0003* (2013.01);
(Continued)

(58) Field of Classification Search
None
See application file for complete search history.

(56) References Cited

U.S. PATENT DOCUMENTS 2,725,677 A    12/1955  Myers
5,084,386 A    1/1992   Tuse et al.
(Continued)

FOREIGN PATENT DOCUMENTS

CN    101979498 A  *  2/2011
JP    H06-071430 B  *  9/1994
(Continued)

OTHER PUBLICATIONS

Santek ("Production of paramylon, a β-1,3-glucan, by heterotrophic growth of Euglena gracilis on potato liquor in fed-batch and repeated-batch mode of cultivation" Eng. Life Sci. 2012, 12 No. 1 89-94, published Dec. 25, 2011).*

(Continued)

*Primary Examiner* — Robert Yamasaki
*Assistant Examiner* — Charles Zoltan Constantine
(74) *Attorney, Agent, or Firm* — Cooley LLP

(57) ABSTRACT

Immune function of an animal can be modulated by administration of a composition that includes algae meal or beta glucan. The algae meal can be made by growing *Euglena* using particular methods and conditions, including certain continuous, semi-continuous, fed-batch, and repeat batch methods in sterile fermenters. *Euglena* provides a form of beta glucan that is different from other organisms, where the beta glucan is predominantly unbranched beta-1,3-glucan. Use of algae meal and beta glucan produced by the disclosed processes can improve the wellbeing of an animal or human, and may augment or even replace the use of antibiotics in certain circumstances.

29 Claims, 22 Drawing Sheets

(51) Int. Cl.
  *C12N 1/10* (2006.01)
  *C12N 1/12* (2006.01)
  *C08L 5/00* (2006.01)

(52) U.S. Cl.
  CPC .............. *C08B 37/0024* (2013.01); *C08L 5/00* (2013.01); *C12N 1/10* (2013.01); *C12N 1/12* (2013.01)

(56) References Cited

U.S. PATENT DOCUMENTS

| | | | |
|---|---|---|---|
| 5,385,382 | A | 1/1995 | Single, II et al. |
| 5,385,832 | A | 1/1995 | Tuse et al. |
| 5,861,383 | A | 1/1999 | Cardin et al. |
| 2003/0203016 | A1 | 10/2003 | Suwelack et al. |
| 2006/0009419 | A1 | 1/2006 | Ross et al. |
| 2010/0239712 | A1 | 9/2010 | Brooks et al. |
| 2010/0303989 | A1* | 12/2010 | Brooks .................. A21D 2/165 426/541 |

FOREIGN PATENT DOCUMENTS

| | | | |
|---|---|---|---|
| JP | 2516031 | B2 * | 7/1996 |
| JP | 2777418 | B2 * | 7/1998 |

OTHER PUBLICATIONS

Anderson ("Microbiology: Algae and the vitamin mosaic" Nature 438, 33-35, 2005, supplementary information).*

Barsanti, L. et al. (2001) "Paramylon(P-1 ,-3-glucan) content in wild type and WZSL mutant of Euglena gracilis. Effects of growth conditions," Journal of Applied Phycology 13:59-65.*

Extended European Search Report mailed on Mar. 31, 2016, for European Patent Application No. 13 788 362.5, filed on May 7, 2013, 8 pages.*

Wu, Y.T. et al. (2008). "The Technology and Application of High-Cell Density Heterotrophic Microalgae Culture" China Food Additives 6(2):66-68, located at , 15 total pages (with English Machine Translation).*

Laura Barsanti, Alessandra Bastianini, Vincenzo Passarelli, Mario R. Tredici & Paolo Gualtieri, Fatty acid content in wild type and WZSL mutant of Euglena gracilis: Effects of carbon source and growth conditions, Journal of Applied Phycology 12: 515-520, 2000, Kluwer Academic Publishers, Netherlands.

Samuel I. Beale, Terrence Foley, and Valdis Dzelzkalns,δ-Aminolevulinic acid synthase from Euglena gracilis, Proc. Natl. Acad. Sci. vol. 78, No. 3, pp. 1666-1669, Mar. 1981, USA.

Bozidar Santek, Michael Felski, Karl Friehs, Martin Lotz, and Erwin Flaschel, Production of paramylon, a β-1,3-glucan, by heterotrophic cultivation of Euglena gracilis on potato liquor, Eng. Life Sci. 2010, 10, No. 2, 165-170, Croatia.

Tomoya Fujita, Hideki Aoyagi, James C. Ogbonna, Hideo Tanaka, Effect of mixed organic substrate on α-tocopherol production by Euglena gracilis in photoheterotrophic culture, Appl Microbiol Biotechnol (2008) 79:371-378, Japan.

James C. Ogbonna & Hideo Tanaka, Cyclic autotrophic/heterotrophic cultivation of photosynthetic cells: A method of achieving continuous cell growth under light/dark cycles, Bioresource Technology 65 (1998) 65-72, Great Britain.

James C. Ogbonna, Shota Tomiyama & Hideo Tanaka, Heterotrophic cultivation of Euglena gracilis Z for efficient production of α-tocopherol, Journal of Applied Phycology 10:67-74, 1998, Belgium.

J.S. Rodriguez-Zavala, M.A. Ortiz-Cruz, G. Mendoza-Hernandez and R. Moreno-Sanchez, Increased synthesis of α-tocopherol, paramylon and tyrosine by Euglena gracilis under conditions of high biomass production, Journal of Applied Microbiology 109, 2160-2172, Mexico, (2010)

Bozidar Santek, Michael Felski, Karl Friehs, Martin Lotz, Erwin Flaschel, Production of paramylon, a β-1,3-glucan, by heterotrophic cultivation of Euglena gracilis on a synthetic medium, Eng. Life Sci. 2009, 9, No. 1, 23-28, Croatia.

Haruko Takeyama, Akihisa Kanamaru, Yuko Yoshino, Hiroyuki Kakuta, Yoshiya Kawamura, and Tadashi Matsunaga, Production of Antioxidant Vitamins, β-Carotene, Vitamin C, and Vitamin E, by Two-Step Culture of Euglena gracilis Z, Biotechnology and Bioengineering, vol. 53, pp. 185-190 (1997), Japan.

Bozidar Santek, Karl Friehs, Martin Lotz, Erwin Flaschel, Production of paramylon, a β-1,3-glucan, by heterotrophic growth of Euglena gracilis on potato liquor in fed-batch and repeated-batch mode of cultivation, Eng. Life Sci. 2012, 12, No. 1, 1-6, Croatia.

Sakagami H., Unten S., Hanaoka A, Ohsawa N., Fujimaki, Chemical modification potentiates paramylon induction of antimicrobial activity, In vivo, vol. 3, Issue 4, 243-7, 1989, Greece.

Sakagami H., Kikuchi K., Takeda M., Sato T., Ichikawa, Macrophage stimulation activity of antimicrobial N,N-dimethylaminoethyl paramylon, In vivo, vol. 5, Issue 2, 101-105, 1991, Greece.

International Search Report mailed on Sep. 20, 2013, for PCT Application No. PCT/US2013/039939, filed on May 7, 2013, 2 pages.

Written Opinion mailed on Sep. 20, 2013, for PCT Application No. PCT/US2013/039939, filed on May 7, 2013, 7 pages.

Barsanti, L. et al. (2001) "Paramylon(β-1,-3-glucan) content in wild type and WZSL mutant of *Euglena gracilis*. Effects of growth conditions," *Journal of Applied Phycology* 13:59-65.

Wu, Y.T. et al. (2008). "The Technology and Application of High-Cell Density Heterotrophic Microalgae Culture" China Food Additives 6(2):66-68, located at <http://www.cnki.net>, 15 total pages (with English Machine Translation).

* cited by examiner

Gas separator configurations of internal-loop ALRs

Gas separator configurations of external-loop ALRs

MULTI-STAGE PROCESS FOR PRODUCTION OF IMMUNE MODULATOR

CROSS-REFERENCE TO RELATED APPLICATIONS

This application claims the benefit of U.S. Provisional Application No. 61/643,572, filed on May 7, 2012. The entire disclosure of the above application is incorporated herein by reference.

INTRODUCTION

This section provides background information related to the present disclosure which is not necessarily prior art.

Beta glucan can function as an immune modulator. The immune system of higher organisms has evolved to recognize beta glucan as it is typically associated with the surface of pathogenic microorganisms. By introducing beta glucan from a non-pathogenic source into the diet of humans and animals, one can, in effect, prime the immune system so that its response to an actual disease challenge is more robust. At the physiological level, beta glucan interacts with cell surface receptors to initiate a cascade of events, including phagocytosis and the production of cytokines such as tumor necrosis factor (TNF)-$\alpha$ and numerous interleukins (IL-2, IL-3, IL-6, IL-10, IL-12). To date, the vast majority of research on beta glucan as an immune modulator has been conducted with beta glucan derived from yeast. Yeast beta glucan contains a mixture of beta-1,3/1,6 linkages and is associated with components of the yeast cell wall that make yeast-derived beta glucan difficult to isolate.

SUMMARY

The present technology includes systems, processes, articles of manufacture, and compositions that relate to growing organisms of the genus *Euglena*, which produce beta glucan and predominantly beta-1,3-glucan.

Methods for growing *Euglena* are provided that include: growing *Euglena* heterotrophically in a growth media; removing a portion of the growth media comprising *Euglena* to form a first removed growth media, the first removed growth media having a *Euglena* concentration of at least about 20 grams dry weight per liter and the *Euglena* having greater than 30% by weight beta glucan and less than 70% by weight beta glucan; and replenishing a portion of the growth media with fresh growth media to form a first replenished growth media. The growing, removing, and replenishing steps can be repeated a plurality of times. The removing step and the replenishing step can be performed simultaneously or the removing step and the replenishing step can be performed sequentially. Algae meal made according to the disclosed methods possesses a surprising and unexpected ability to modulate the immune system of animals.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 12:
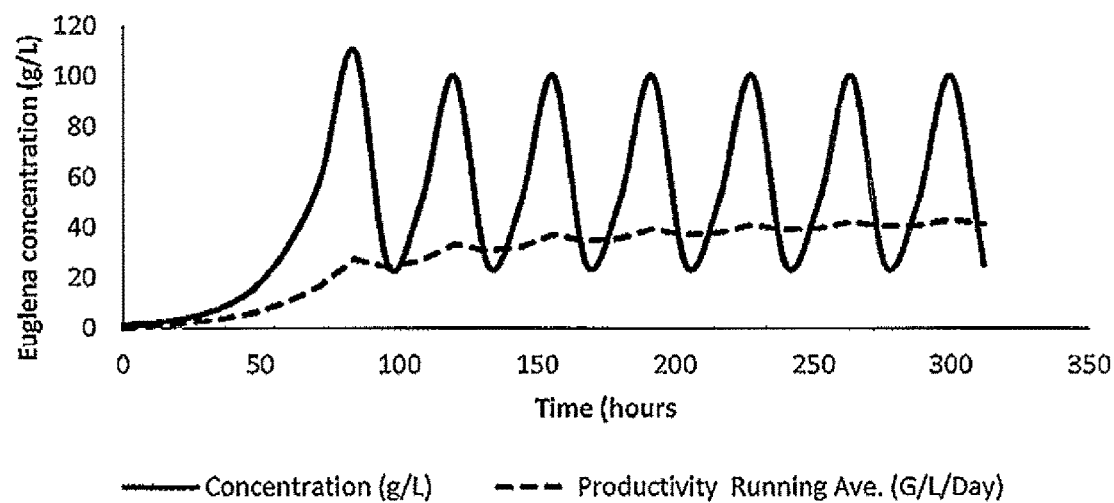

FIG. 12 graphically depicts *Euglena* concentration in a repeat batch growth process according to the present technology.

Figure 13:
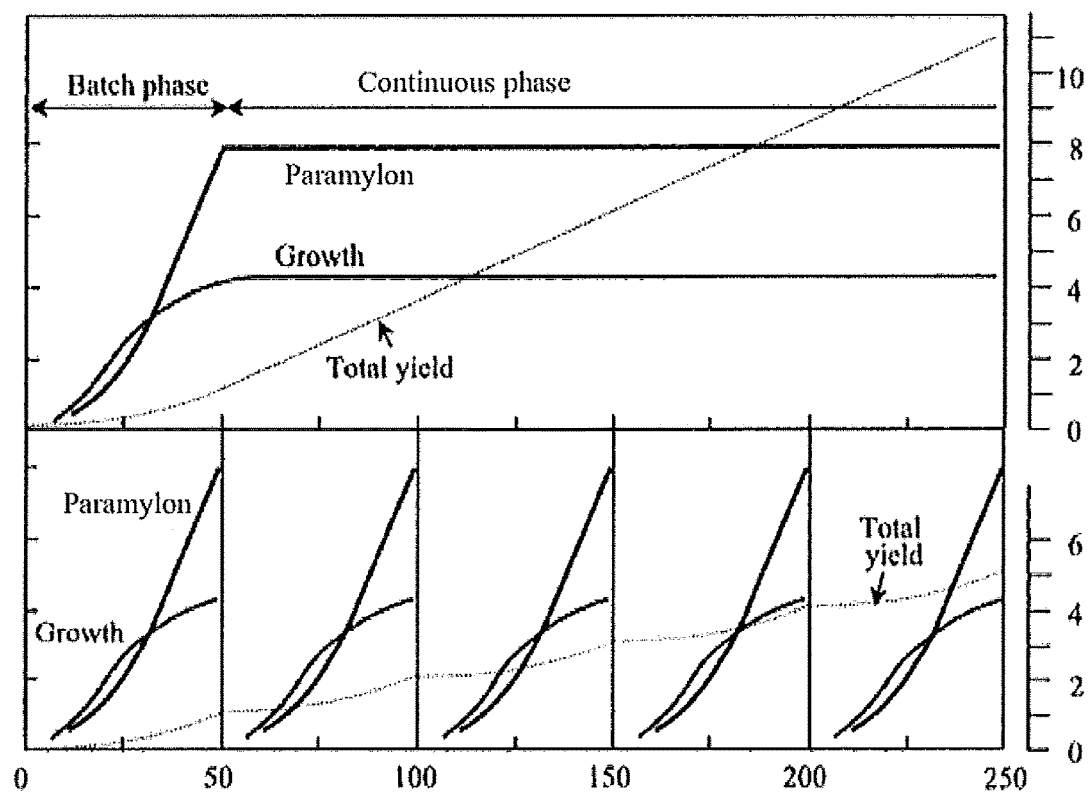

FIG. 13 graphically depicts *Euglena* concentration in a continuous batch growth process according to the present technology.

Figure 14:
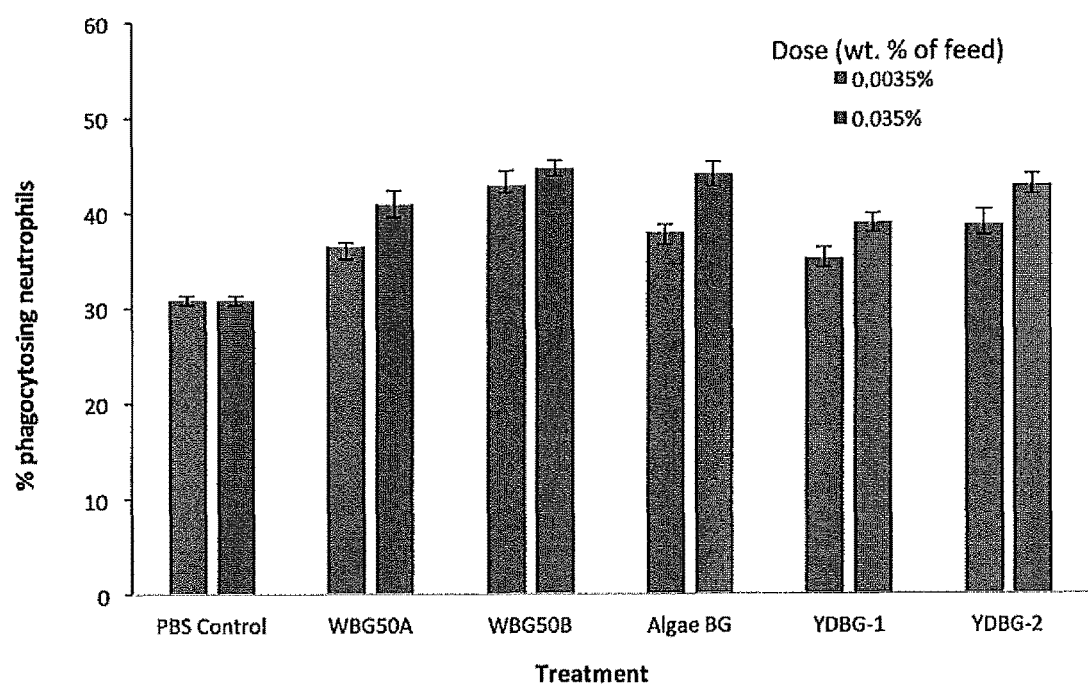

FIG. 14 graphically depicts the phagocytosis index of mouse neutrophils sampled from peripheral blood 48 hours post beta glucan treatment. Bars represent means ($\pm$SE), (n=3 mice). With respect each pair of bars, the left bar represents a dose of 0.0035 wt. % of feed and the right bar represents a dose of 0.035 wt. % of feed.

Figure 15:
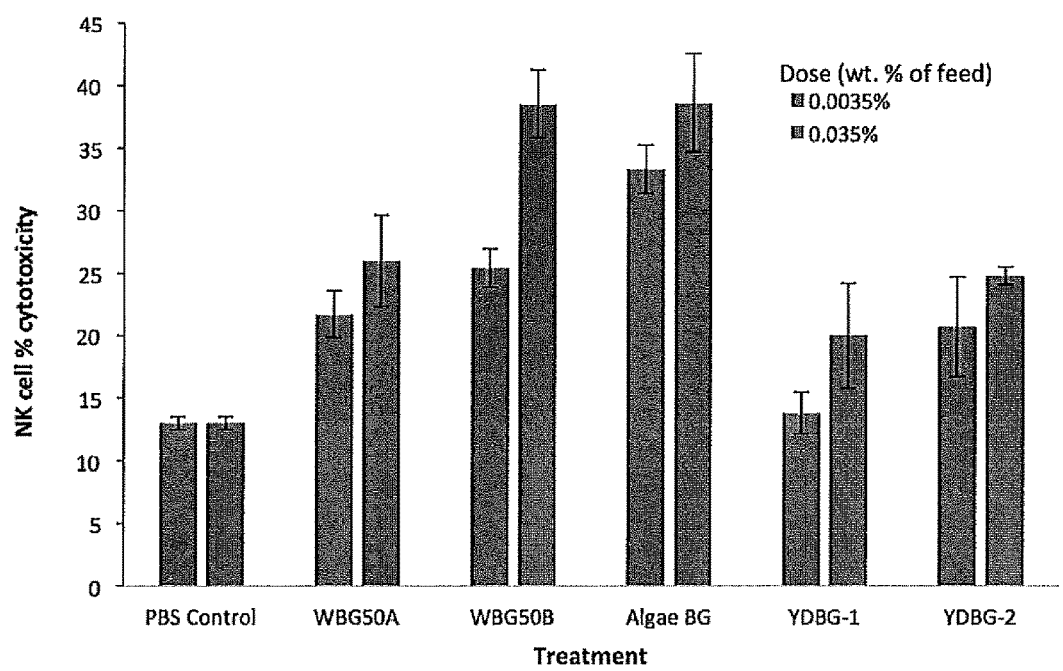

FIG. 15 graphically depicts Natural killer (NK) cell activity of spleen cells harvested 48 hours post beta glucan treatment. With respect each pair of bars, the left bar represents a dose of 0.0035 wt. % of feed and the right bar represents a dose of 0.035 wt. % of feed.

Figure 16:
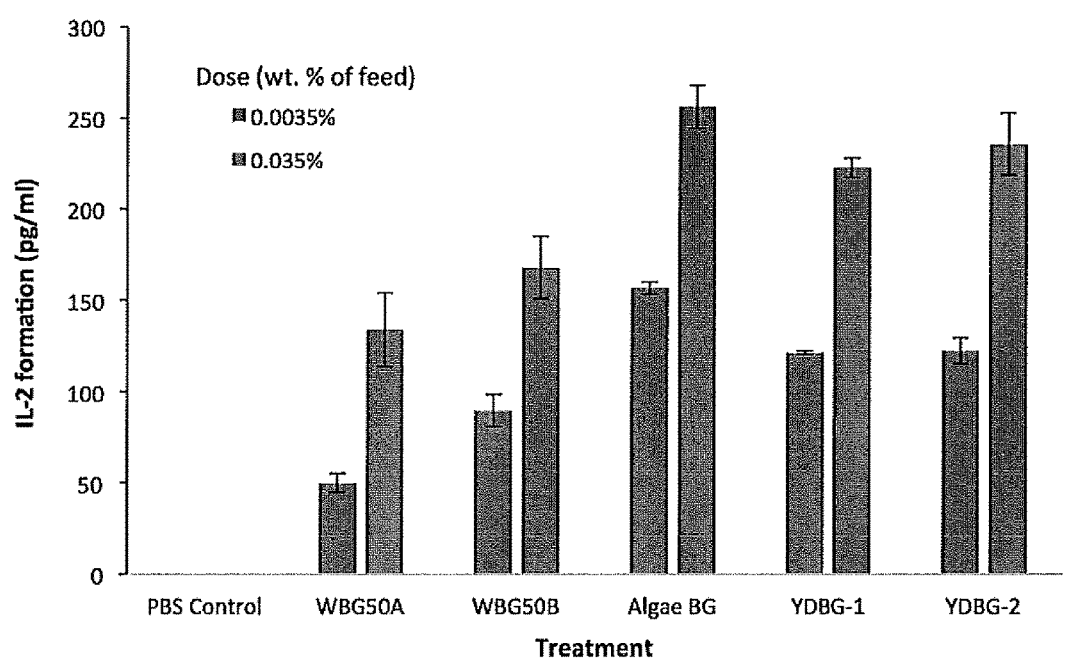

FIG. 16 graphically depicts IL-2 (cytokine) formation (by ELISA) in mice 48 hours post glucan treatment. Bars represent means ($\pm$SE), (n=3 mice). With respect each pair of bars, the left bar represents a dose of 0.0035 wt. % of feed and the right bar represents a dose of 0.035 wt. % of feed.

Figure 17:
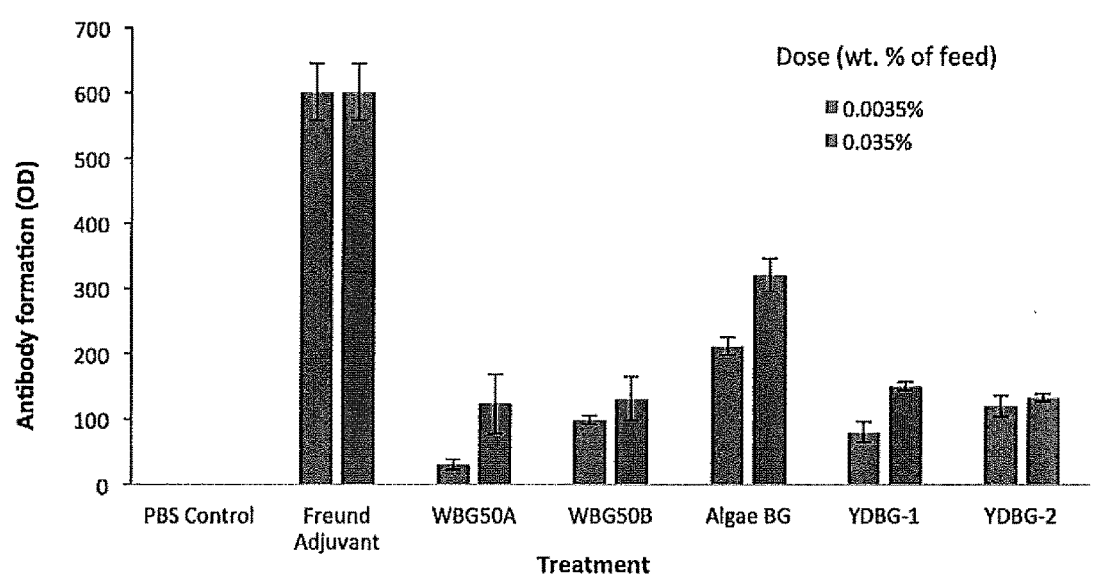

FIG. 17 graphically depicts antibody formation following ovalbumin injection and daily dosing of beta glucan treatments. Bars represent means ($\pm$SE), (n=3 mice). With respect each pair of bars, the left bar represents a dose of 0.0035 wt. % of feed and the right bar represents a dose of 0.035 wt. % of feed.

Figure 18:
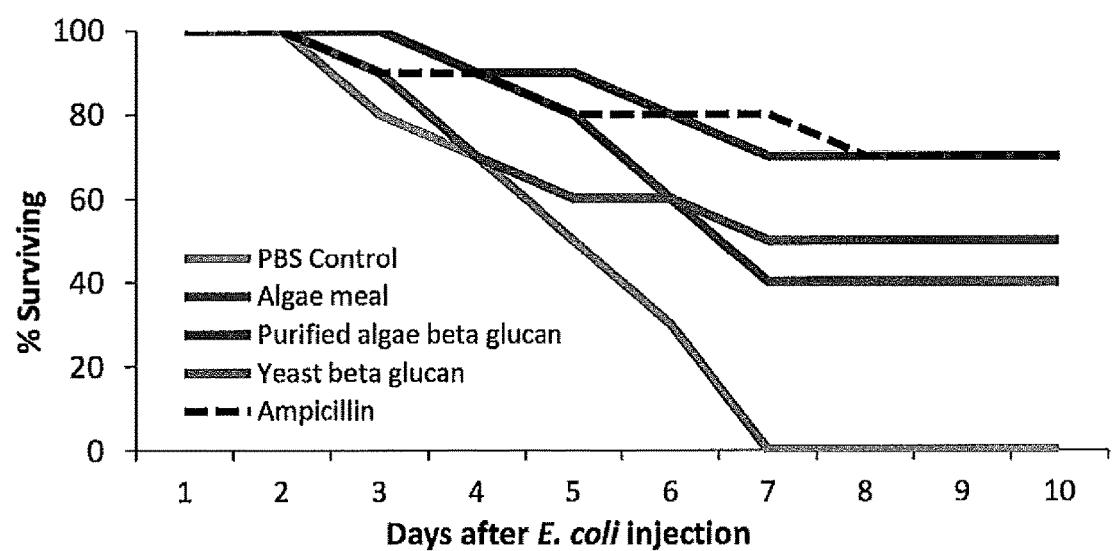

FIG. 18 graphically depicts survivorship of mice following an injection of *E. coli* on day 0. Algae meal, purified algae beta-1,3-glucan, and yeast-derived beta glucan were fed orally by gavage for 5 days at a dose equivalent to 0.01% of the daily feed ration starting 2 days before the *E. coli* injection (day −2). The PBS control group was given just a PBS gavage while the antibiotic treatment group was given 13 mg/kg of Ampicillin orally on days 0 through 4. n=10 mice per treatment group. The dashed line represents Ampicillin and the highest to lowest lines as viewed on the far right of the graph (i.e., days 7-10) represent purified algae beta-1,3-glucan, algae meal, yeast beta glucan, and PBS control, respectively.

Figure 19:
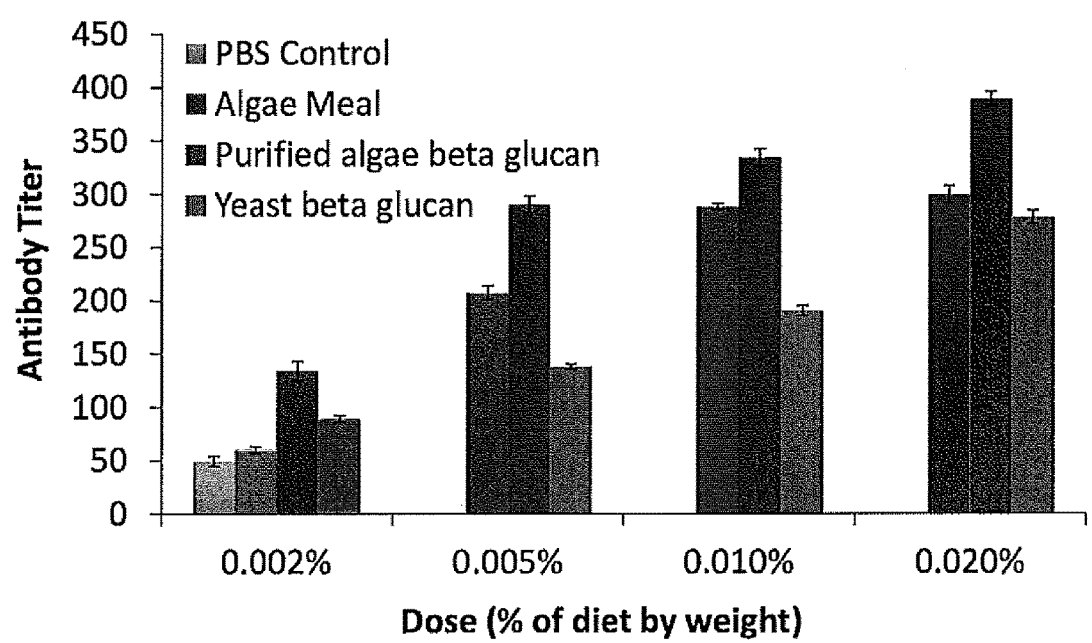

FIG. 19 graphically depicts antibody formation following ovalbumin injection (day 3 and 16) and daily dosing of beta glucan treatments for 23 days. The negative control received ovalbumin but no beta glucan. Bars represent means±standard error. n=3 mice per treatment group. Each group of bars represents, from left to right, PBS control, algae meal, purified algae beta glucan, and yeast beta glucan. Note that PBS control values are only shown for the 0.002% dose.

Figure 20:
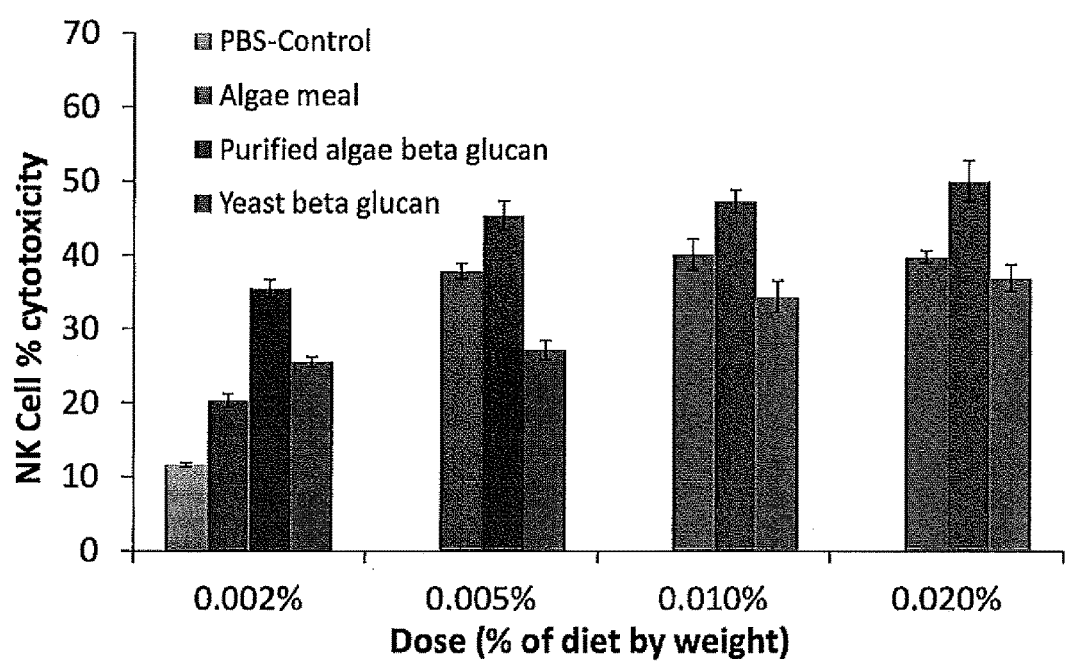

FIG. 20 graphically depicts Natural killer (NK) cell activity of spleen cells harvested on day 14. Bars represent means±standard error. n=3 mice per treatment group. Each group of bars represents, from left to right, PBS control, algae meal, purified algae beta glucan, and yeast beta glucan. Note that PBS control values are only shown for the 0.002% dose.

Figure 21:
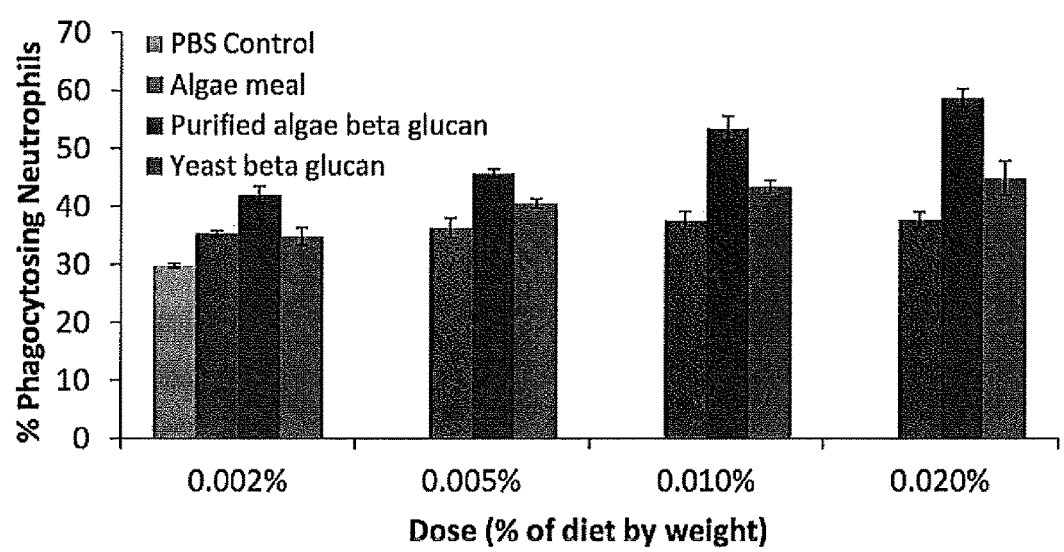

FIG. 21 graphically depicts the phagocytosis index of mouse neutrophils sampled from peripheral blood on day 14. Bars represent means±standard error. n=3 mice per treatment group. Each group of bars represents, from left to right, PBS control, algae meal, purified algae beta glucan, and yeast beta glucan, Note that PBS control values are only shown for the 0.002% dose.

Figure 22:
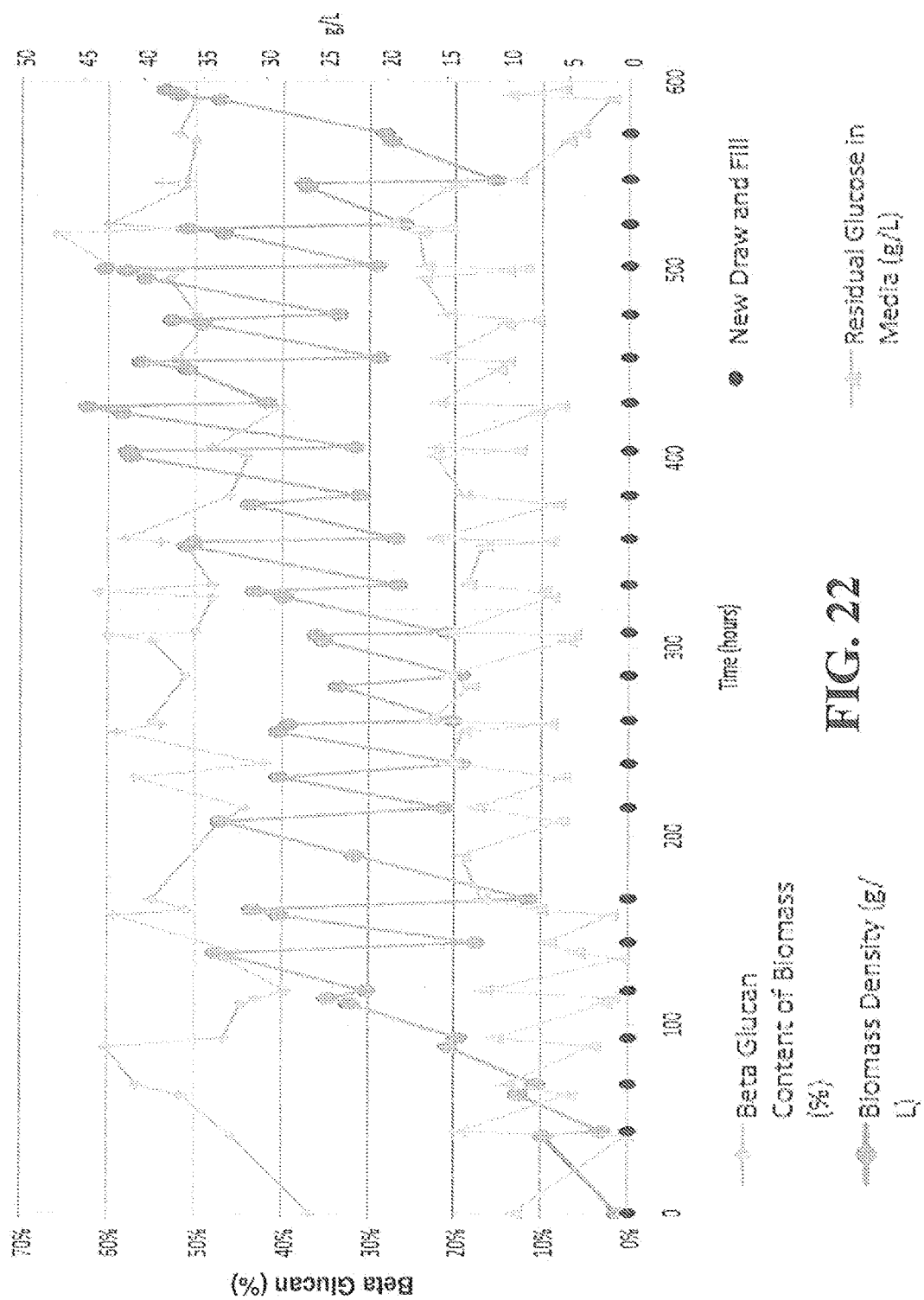

FIG. 22 graphically depicts beta glucan, *Euglena* biomass density, timing of removals and replenishments, and residual glucose in the growth media during a repeat batch growth process according to the present technology.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Regarding the methods disclosed, the order of the steps presented is exemplary in nature, and thus, the order of the steps can be different in various embodiments where possible. Except in the examples, or where otherwise expressly indicated, all numerical quantities in this description indicating amounts of material or conditions of reaction and/or use are to be understood as modified by the word "about" in describing the broadest scope of the technology.

Disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

The present technology includes systems, processes, articles of manufacture, and compositions that relate to growing algae, including *Euglena* sp., and specifically *Euglena gracilis*. *Euglena* can be heterotrophically grown to cell densities at or above 20 to 60 grams of dry weight biomass per liter of growth media. *Euglena* grown at such densities can be more economical for commercial production of beta glucan and algae meal containing beta glucan than photosynthetic methods of growing *Euglena*. Unlike yeast-derived beta glucan, *Euglena* produce beta glucan containing almost entirely beta-1,3 linkages, where the beta glucan is readily bioavailable with little or no processing of the *Euglena* cell, and where the beta glucan can also be easily extracted and purified, if desired. *Euglena* biomass (algae meal) or *Euglena*-derived beta glucan products produced using the present methods and systems demonstrate surprising and unexpected results in modulating the immune system of animals.

The structure of beta glucan derived from *Euglena* is different from beta glucans from other organisms. One major difference is that while other organisms produce beta glucans incorporated into their cell wall, the genus of protists known as *Euglena* can produce beta glucan, including a particulate form of beta glucan, known as paramylon, that is not incorporated into the structure of the cell wall. Rather, *Euglena* accumulates beta glucan as a water-insoluble granule in the cytoplasm and utilizes this form of beta glucan as a form of carbohydrate energy storage.

Various aspects of the present technology include cultivation, concentration, and (hying of whole cell *Euglena* sp. microorganisms for use as additives in food and feed products. Optionally, the paramylon may be extracted from the *Euglena* using a physical and chemical separation process that has certain advantages over other processes. While various substances such as alpha tocopherol, astaxanthin, or paramylon can be extracted from *Euglena*, the present technology provides an efficient, cost-effective platform for cultivation of whole-cell *Euglena* (algae meal) to be used as a food ingredient or as a feedstock substance for further extraction of highly purified paramylon. The algae meal and extracted beta glucan also provide special properties, including the ability to modulate the immune system of an animal, as further described herein.

Reducing the cost of producing *Euglena* and *Euglena*-derived paramylon makes *Euglena* a suitable organism for large scale commercial production of valuable compounds. For example, it has been suggested that *Euglena* may a natural source for producing affordable alpha tocopherol, a valuable form of Vitamin E (See Ogbonna et al.; Journal of Applied Phycology 10:67-74, 1998). *Euglena* is also a source of beta-1,3-glucan or paramylon, a polysaccharide with applications as an immunomodulator in food products, nutraceuticals, cosmetics, beverages, and animal feed applications. Beta-1,3-glucan from yeast is known to enhance innate immune system activity in animals and humans (e.g., U.S. Pub. No. 2006/0009419 to Ross et al.). There are different forms of beta-1,3-glucans, including variations in branching, solubility and molecular weight that affect the ultimate binding affinity and efficacy in subjects. The beta-1,3 glucan from *Euglena* can be a cost-effective source of beta-1,3-glucan when produced on a larger scale. *Euglena* can accumulate beta-1,3-glucan as cytoplasmic granules that together are between 30-90% of the total cell mass. Yeast-based glucans, in contrast, typically comprise less than 15% of the total organism mass and are bound into the cell wall, requiring additional extraction in order to reach comparable biological activity when dosed orally or intravenously to animals. The result is that yeast-based glucans can typically range in price from $50 to over $300 per kilogram. At the same time, highly purified paramylon from *Euglena* is available, but only in small quantities and at high prices; e.g., over $50,000 per kilogram (see Sigma Aldrich Catalog online at www.sigmaaldrich.comicatalog/productisigma/ 89862?lang=en&region=US).

Attempts to grow *Euglena* include bench top scale fermentation methods, methods using photosynthesis as at least a part of the growth process, and methods optimizing the production and extraction of Vitamin E or paramylon. However, in scaling up a process for growth of *Euglena* certain contamination issues and oxygen transfer issues should be considered, which are typically not problems faced at the bench top scale. Drivers for reducing the cost of *Euglena* cultivation can include further increasing the growth rate, increasing the conversion efficiency from a carbon source (e.g., sugar) to biomass, increasing the density of cultivation, increasing the duration of the batch length, and increasing the size of the vessels that the *Euglena* is cultivated in as a means of reducing labor costs.

Paramylon therefore is not commercially produced because cost effective production techniques for *Euglena* have not been developed. By lowering the cost of production, the applications for beta glucans can expand dramatically. For example, beta glucans may be incorporated as an immune-stimulating food or beverage ingredient, as a low-cost nutraceutical, or as an animal or aquaculture feed additive, where beta glucans may even be used as a replacement for antibiotics. The ability to supplement or replace antibiotics is particularly interesting because the use of antibiotics in animal production as an infection prevention mechanism is increasingly criticized for the role it may play in the creation of antibiotic-resistant "superbugs," such as MRSA. *Euglena*-derived beta-1,3-glucan may also be used as a cosmetic ingredient, wound dressing, or even an immune-stimulating drug ingredient or precursor to a drug to be used to provide enhanced innate immune system defense. An activated immune system requires additional caloric expenditure, and beta-1,3-glucan can therefore even be used to simultaneously boost innate immune system activity while also boosting general metabolism in weight-loss applications. There are many applications and people that may benefit from access to a more affordable form of beta glucan than what is commercially available.

Efforts to grow *Euglena* have resulted in cell densities ranging from about 0.5 to 50 grams per liter. For example, the method of *Euglena* growth described in U.S. Pat. No. 5,084,386 claims a carbon source specified at 4 g/L to 16 g/L of carbon. The total concentration of all dissolved components mentioned in the specifications was less than 45 g/L. Therefore, it would have been highly unlikely for this growth technique to result in a concentration of *Euglena* greater than 45 g/L. In reality, the concentration of *Euglena* biomass that was grown was probably much less given the conversion efficiency from the carbon source (glucose) to *Euglena* biomass, which is typically about 0.5 to 0.9 gram biomass per gram of glucose consumed.

Other efforts to grow *Euglena gracilis* have resulted in beta-1,3-glucan concentrations up to 70%, as measured by the dry weight proportion of beta-1,3-glucan relative to the dry weight of the total biomass, at higher densities and cell doubling time than has been previously described. This is an important development for industrial applications. For example, Santek et al. produced *Euglena* at densities of 13-14 g/L with paramylon mass fractions of 50-60% g/L in a single batch by using a synthetic medium containing 15 g/L of glucose as the main carbon source (Engineering Life Sci. 2009, 9, No. 1, 23-28). Santek et al. also achieved about 20 g/L biomass density using a repeated batch cultivation method with potato processing wastewater as a major media ingredient; a paramylon mass fraction of about 75% was obtained (Engineering Life Sci. 2012, 12). Rodriguez-Zavala et al, produced *Euglena* in a single batch at densities of 10.8 g/L after experimenting with several carbon sources (Journal of Applied Microbiology 109, 2160-2172). Ogbonna achieved 39.5 g/L *Euglena* by using a single-stage jar fermentation apparatus, although this was not performed at a commercial scale or with a multi-stage bioreactor system (Journal of Applied Phycology 10: 67-74, 1998). Ogbonna was more interested in α-tocopherol production by *Euglena* and did not measure the beta glucan mass fraction in the biomass. However, none of these efforts employed a multistage or continuous bioreactor process for cultivating *Euglena* at commercial scales, and none have reached an economic production density greater than 50 grams per liter. Finally, none have used a simple and low-cost media formulation that can be reproducibly and consistently prepared (unlike the potato wastewater used by Santek et al.).

Further efforts failed to grow *Euglena gracilis* at higher densities because they utilized single batch processes where all nutrients and carbon sources were added during the beginning of the growth stage, prior to, or immediately after inoculation (e.g., U.S. Pat. No. 5,084,386). These efforts also utilized a single-stage bioreactor. Moreover, these efforts used small reaction chambers less than 100 liters in volume that were not capable of producing economically meaningful volumes of *Euglena* and which did not face many of the most difficult problems in scaling up an industrial bioprocess, such as optimization of the tradeoff between maximizing oxygen transfer rates and minimizing the deleterious effects of shear stress that occur with mechanical agitation of large, sensitive cells such as *Euglena*. Finally, it was determined that these efforts did not add sufficient carbon source or nutrient concentrations to reach *Euglena* densities reaching more than 40 grams per liter.

*Euglena* has a slow cell division time relative to some other microorganisms. For example, the generation time of *Euglena* in optimal conditions can be about 12 hours. In contrast, the generation time of bacteria grown under optimal conditions can be as fast as 20 minutes. Without an industrial production method that can be used to manage the ability of faster growing undesirable contaminant organisms, *Euglena* has not been grown at large enough volumes and high enough concentrations in order to be economically viable.

Algae in general have been grown in phototrophic and heterotrophic conditions. However, the vast majority of algae grown heterotrophically have been oil-rich species, and the growth conditions of the surrounding process were tailored to produce large quantities of oils, such as Omega 3 oils or other oils that can be combusted as liquid biofuels. Some algae can produce oil in quantities greater than 80% as measured by the proportion of oil to the dry weight of the algae biomass. *Euglena*, in contrast, is an oil-poor species, with generally less than 15% of the total biomass being comprised of oils or other lipids.

Although others have explored the production of *Euglena* at a very basic level, this production has been at the lab scale in single-stage growth vessels—usually in small flasks or carboys in a single batch. As a result, *Euglena* has not been produced in larger quantities that would make it useful for commercial applications. In addition, much of the research with respect to growing *Euglena* has used *Euglena* as source for alpha tocopherol. The optimal growth conditions for the production of these compounds are not necessarily the same optimal conditions for the production and potential extraction of beta glucan from *Euglena*.

The present technology includes methods for growing *Euglena* (e.g., *Euglena gracilis*) using a multi-stage heterotrophic process in bioreactors larger than 500 liters in volume and at densities greater than 20-60 grams per liter and up to more than 200 grams per liter. By applying the described multi-stage, fed-batch and repeat draw and fill processes for growing *Euglena* at this scale, production economics for *Euglena*-derived beta glucans can be achieved that are superior to the production economics for comparable extracted and purified yeast-derived beta glucans.

The present technology includes methods for growing *Euglena* cells in the dark using heterotrophic processes that contain a sufficient carbon source to produce biomass in concentrations greater than 20 to 60 g/L on a dry weight basis. This is achieved by adding the carbon source over time, such that the concentration of available carbon source in the media never exceeds 30 g/L. The carbon source can be added at least three times per batch and can be added in a periodic or continuous fashion.

Other growth methods for *Euglena* do not provide a means for preventing contamination of *Euglena* at an industrial scale. Contamination by foreign cells is not always a critical issue in shorter growth periods, such as in a bench top scale flask or bioreactor. Low pH levels disclosed in other growth methods were likely sufficient enough to keep certain contamination at bay. However, failure to appropriately guard against contamination at an industrial scale is a critical problem that can prevent economic scale and batch runs. Furthermore, yeast and other contaminating organisms may evolve that are capable of outgrowing *Euglena*, even in low pH growth conditions, if additional precautions are not taken. In order to prevent contamination of the *Euglena* population with faster growing organisms like yeast or bacteria, a sterile filter can be employed for the addition of the media or media can be sterilized with steam. This media can be prepared in a liquid form and stored in one or more tanks. Different components of the media may also be stored in different tanks in order to prevent contamination by outside organisms. The media can be heat-sterilized prior to filtering and combining, with care given not to overheat the sugar-containing media lest risking caramelization.

Figure 1:
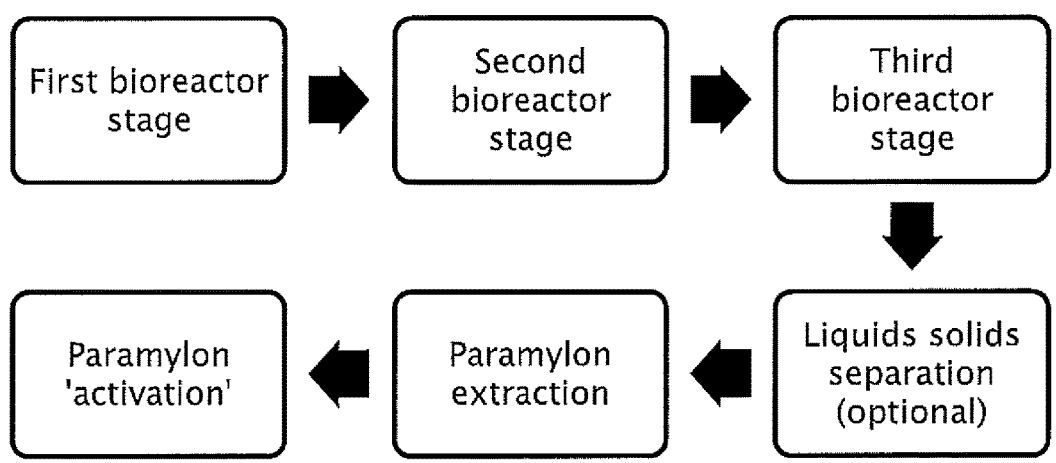
FIG. 1 illustrates a first embodiment of a process for growing *Euglena* according to the present technology.
Figure 2:
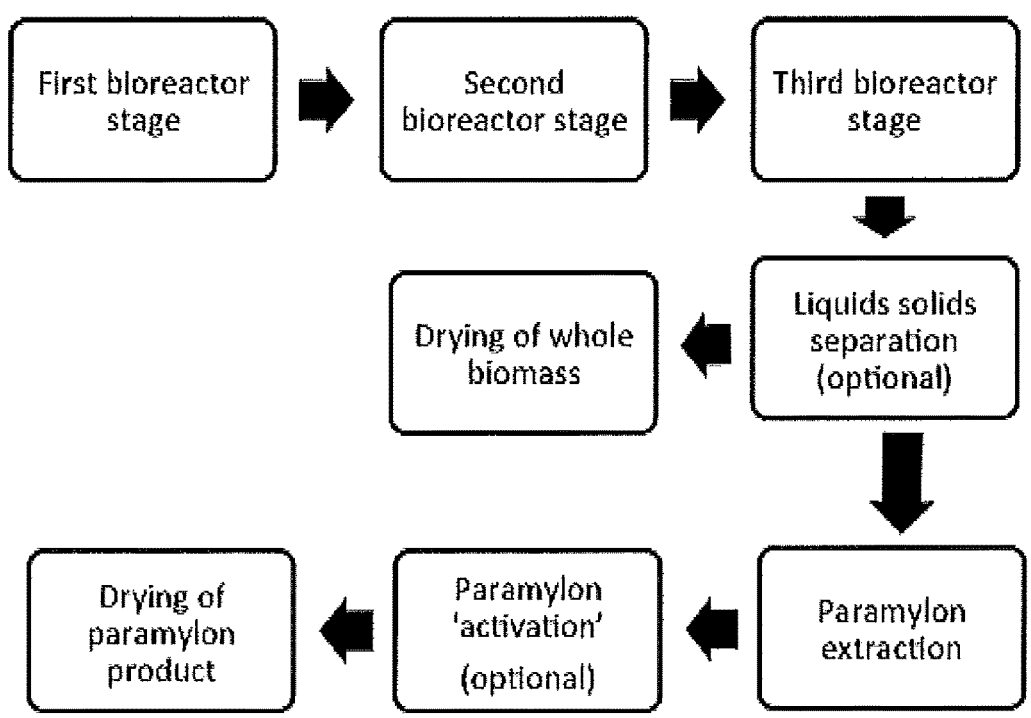
FIG. 2 illustrates a second embodiment of a process for growing *Euglena* according to the present technology.
Figure 3:
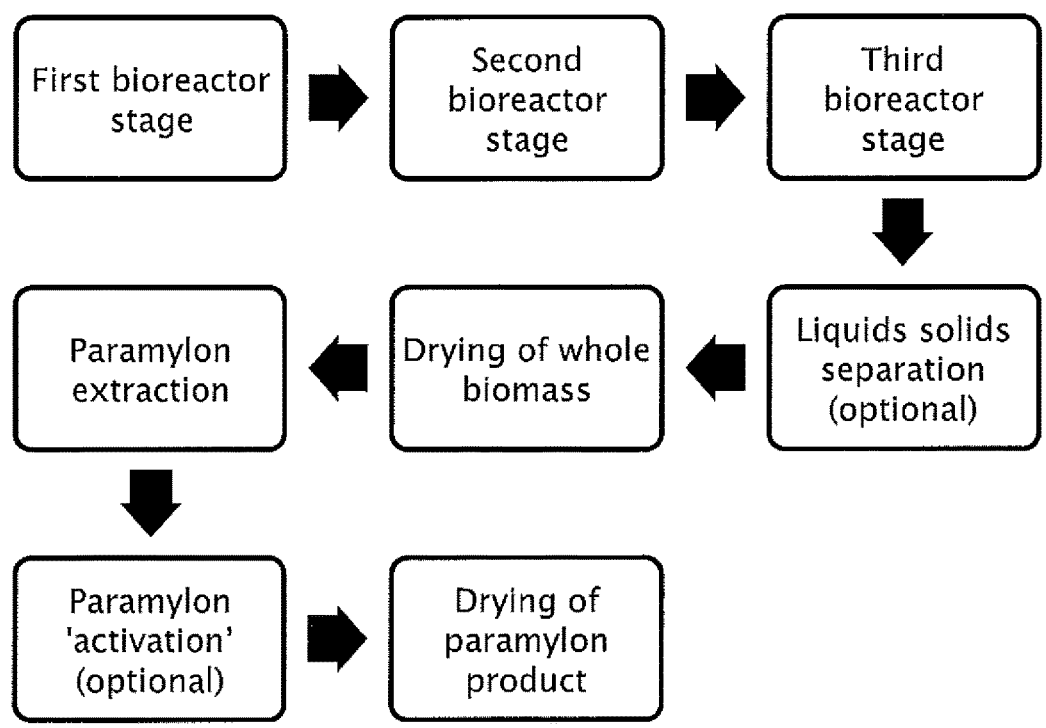
FIG. 3 illustrates a third embodiment of a process for growing *Euglena* according to the present technology.
Figure 4:
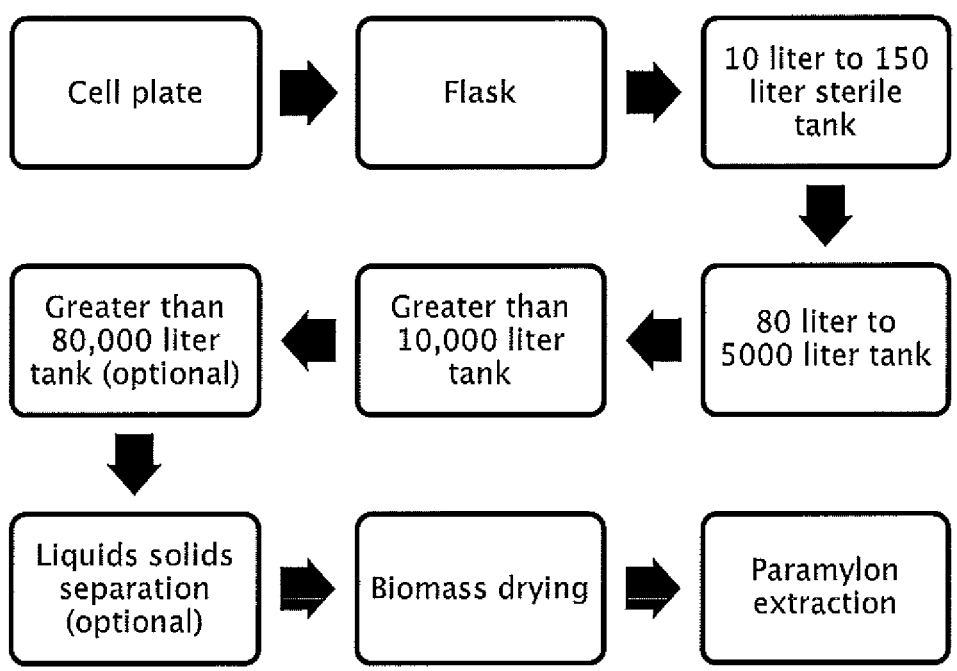
FIG. 4 illustrates a fourth embodiment of a process for growing *Euglena* according to the present technology.
Figure 5:
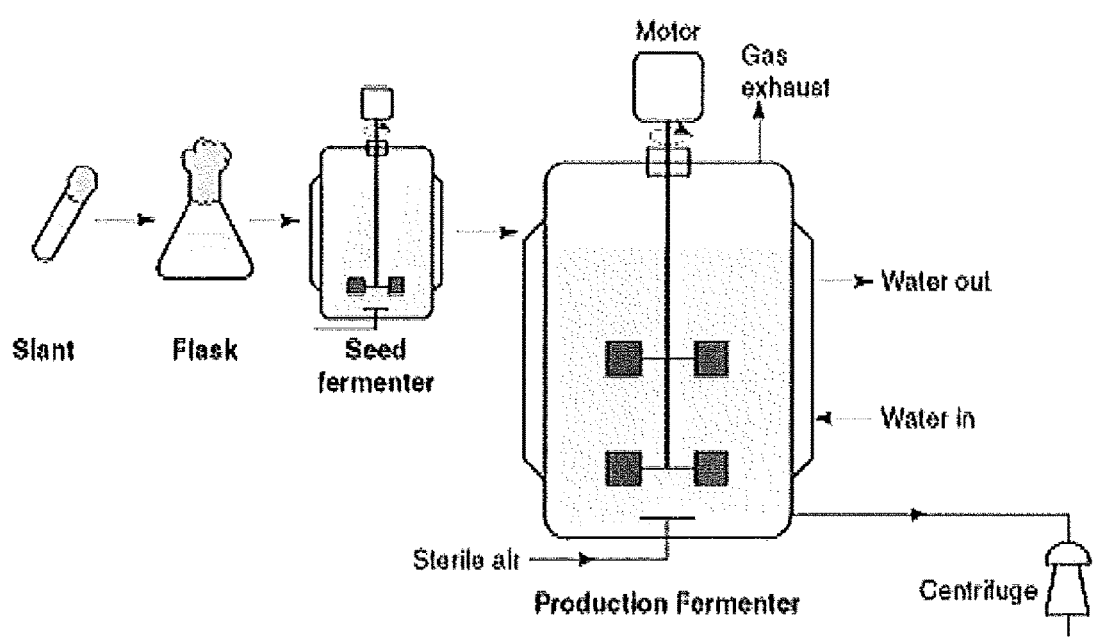
FIG. 5 illustrates a first embodiment of a system for growing *Euglena* according to the present technology.
Figure 6:
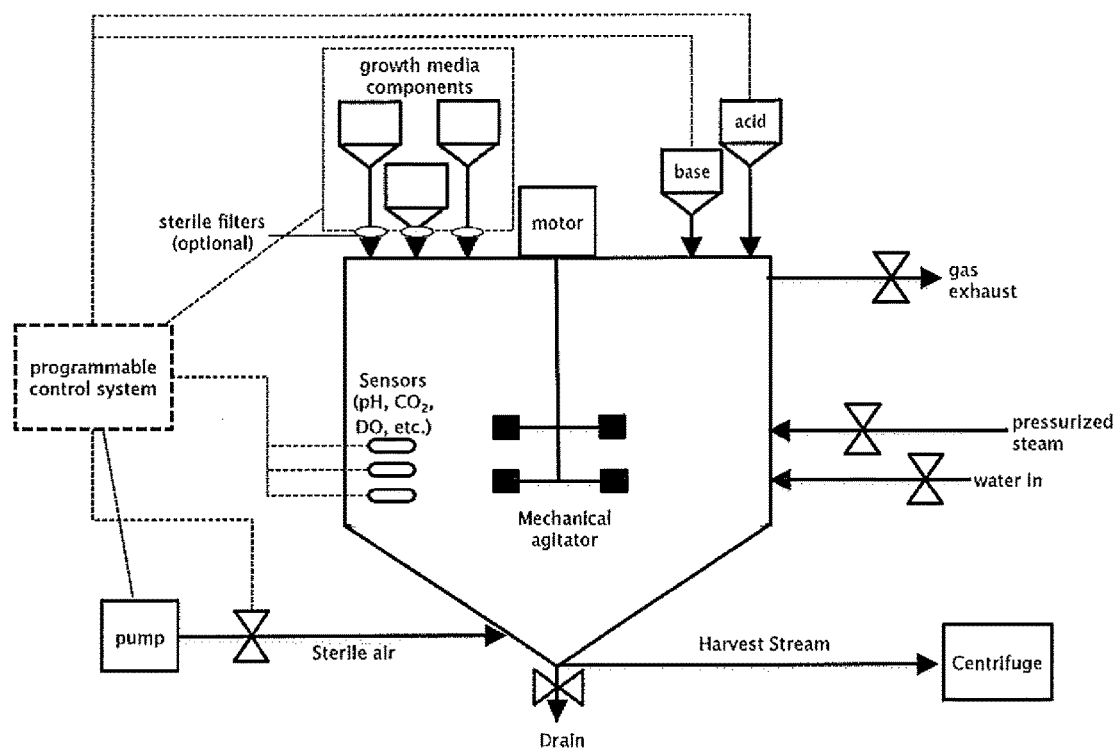
FIG. 6 illustrates a second embodiment of a system for growing *Euglena* according to the present technology.
Figure 7:
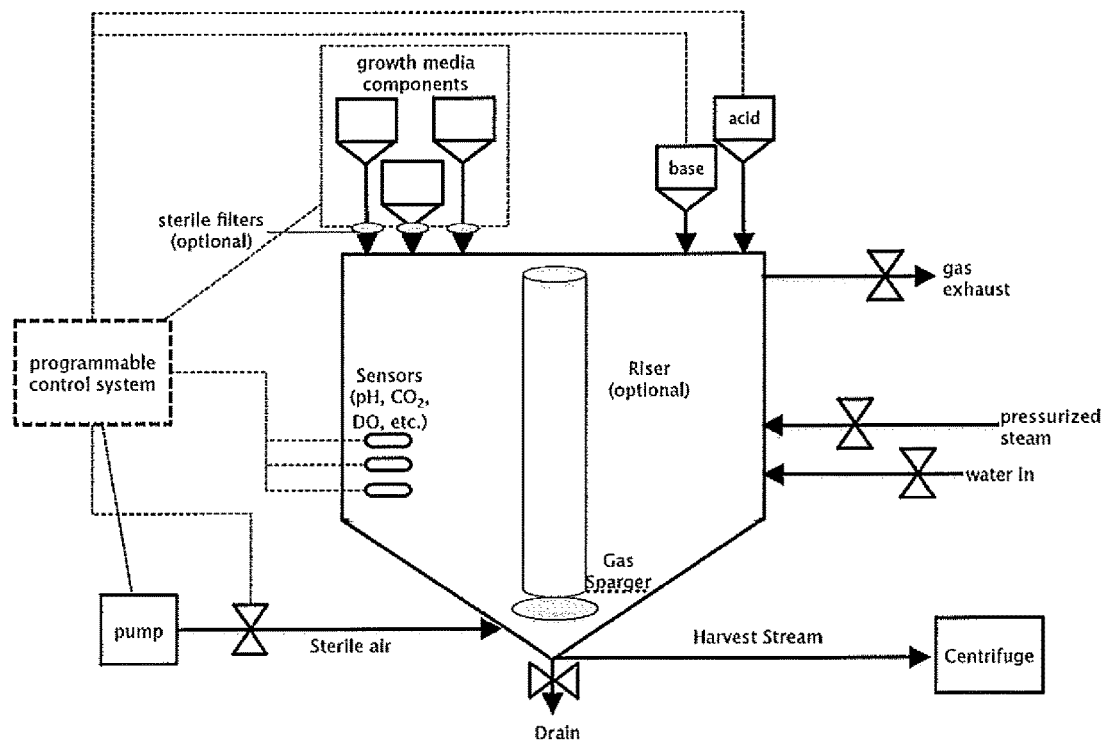
FIG. 7 illustrates a third embodiment of a system for growing *Euglena* according to the present technology.

Although aspects of the present technology can be performed in a single bioreactor that is at least a 1,000 L tank, the preferred means is a multi-stage process, where multiple bioreactors are used in sequence, and where each bioreactor has more bioreactor volume than the bioreactor in the preceding step. Flow charts of certain methods for growing *Euglena* are shown in FIGS. 1, 2, 3, and 4 and schematics of certain systems for growing *Euglena* are shown in FIGS. 5, 6, and 7. For example, a first bioreactor stage may consist of an Erlenmeyer-style or other flask that is oxygenated through surface diffusion on a rotating or gyrating shaker table or magnetic stir bar. This bioreactor may be heated as through a heated table or in a climate controlled atmosphere, usually within a covered incubator device. A heated shaker table such as the New Brunswick Scientific Innova 4000 Heated Desktop Incubator is an example of a device that combines heating and the capability to oxygenate the flask by providing sufficient movement to agitate the surface of the growth media.

A second bioreactor stage may then use a bioreactor chamber that is up to 100 times larger than the first, to which the contents of the first bioreactor stage are transferred and subsequently diluted such that the initial concentration of *Euglena* is in the range of 0.1 to 10 grams per liter. The contents of the first bioreactor stage may be filtered or the *Euglena* may otherwise be concentrated prior to transfer to the second stage, but this is optional. This bioreactor is closed to the atmosphere during operation with the exception of controlled vents, an input for aeration or oxygenation and an input tube or pipe for pumping in the dissolved media. The inputs for pumping dissolved media may also include a sterile filter, typically with a pore size of less than 0.2 microns, in order to prevent undesirable non-*Euglena* microorganisms from entering the chamber. The tank in the second bioreactor stage typically is made from metal or glass, and it is cleaned and disinfected between batches using either steam, heat, or a disinfectant such as ethanol, bleach, or another chemical. This bioreactor stage typically receives additional oxygen from outside the tank either through aeration, or by receiving additional liquid whereby pressurized oxygen has been pre-dissolved into the liquid. Air may also be enriched with oxygen prior to being pumped into the tank. This bioreactor also may have a mechanism to provide stirring and/or mixing of the algae biomass inside of the tank.

*Euglena* may be harvested from the second bioreactor stage. However, the contents of the second bioreactor stage may also be transferred to a third bioreactor stage with volume ranging from 1 to 100 times greater than the second bioreactor stage. This third bioreactor stage can be carried out in a tank with a volume ranging from 1,000 liters to 100,000 liters. This bioreactor is typically closed to the atmosphere during operation with the exception of controlled vents, an input for aeration or oxygenation and an input tube or pipe for pumping in the dissolved media. The inputs for pumping dissolved media may also include a sterile filter, typically with a pore size of less than 0.2 microns, in order to prevent undesirable non-*Euglena* microorganisms from entering the chamber. The tank in the third bioreactor stage typically is made from metal or glass, and it is cleaned and disinfected between batches using either steam, heat, or a disinfectant such as ethanol, bleach, or another chemical. This bioreactor stage typically receives additional oxygen from outside the tank either through aeration, or by receiving additional liquid whereby pressurized oxygen has been pre-dissolved into the liquid. Air may also be enriched with oxygen prior to being pumped into the tank. This bioreactor also may have a mechanism to provide stirring and/or mixing of the algae biomass inside of the tank.

*Euglena* may be harvested directly from the third bioreactor stage. However, the contents of the third bioreactor stage may also be transferred to a fourth bioreactor stage with volume ranging from 5 times to 100 times greater than the second bioreactor stage. This fourth bioreactor stage is likely to be carried out in a tank with a volume ranging from 10,000 liters to 1,000,000 liters. This bioreactor is typically closed to the atmosphere during operation with the exception of controlled vents, an input for aeration or oxygenation and an input tube or pipe for pumping in the dissolved media. The inputs for pumping dissolved media may also include a sterile filter, typically with a pore size of less than 0.2 microns, in order to prevent undesirable non-*Euglena* micro-organisms from entering the chamber. The tank in the fourth bioreactor stage typically is made from metal or glass, and it is cleaned and disinfected between batches using either steam, heat, or a disinfectant such as ethanol, bleach, or another chemical. This bioreactor stage typically receives additional oxygen from outside the tank either through aeration, or by receiving additional liquid whereby pressurized oxygen has been pre-dissolved into the liquid. Air may also be enriched with oxygen prior to being pumped into the tank. This bioreactor also may have a mechanism to provide stirring and/or mixing of the algae biomass inside of the tank.

After transfer to the last bioreactor stage, a *Euglena* batch is cultivated for a time period ranging from 36 to 120 hours before a major portion of the biomass is harvested. In one embodiment, the entire contents of the bioreactor are harvested after this time period. In this embodiment, a single batch is harvested from the last bioreactor stage for each inoculant it receives from the previous bioreactor stage.

In each of the bioreactor stages there is a desirable pH level ranging from 2 to 6, with the most desirable level ranging from 3 to 4. This pH is favorable to *Euglena*, but is lower than the optimal growth conditions for most bacteria. The desirable pH level may be achieved in several ways. First, pH may be manually monitored and acid or base may be periodically be added manually in order to reached the desired pH. Second, pH may be measured in real time with a pH sensor that is in fluid connection with an automated control system, where the automated control system controls pumps, hoppers, or other devices that can automatically add acid or base in order to reach a desired pH that is programmed into the automated control system. Third, in some cases additional acid or base may not need to be added over the course of the reaction. In this case, metabolic processes of the *Euglena* may sufficiently lower the pH into the desired range. Fourth, a conjugate acid-base buffer system may be used in order to help maintain the pH in the target range. Although there are many conjugate acid-base buffer systems that may function appropriately in the target range, an example of an acid buffer system that may be considered to be most favorable maintains a pH range between 2 and 5. One example of such a buffer system is the citrate buffer system. The buffer system may be added at the beginning of the reaction in sufficient quantity such that metabolic processes or other chemicals produced over the course of the biological growth period do not alter the pH outside of the range of the conjugate buffer system.

Figure 8:
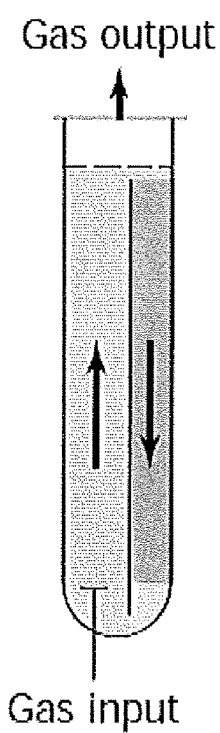
FIG. 8 illustrates embodiments of an internal-loop split air-lift reactor (ALR), an internal-loop concentric tube ALR, and an external-loop ALR for use in the present technology.
Figure 8:
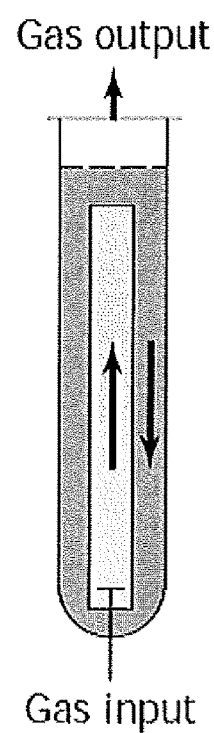
Figure 8:
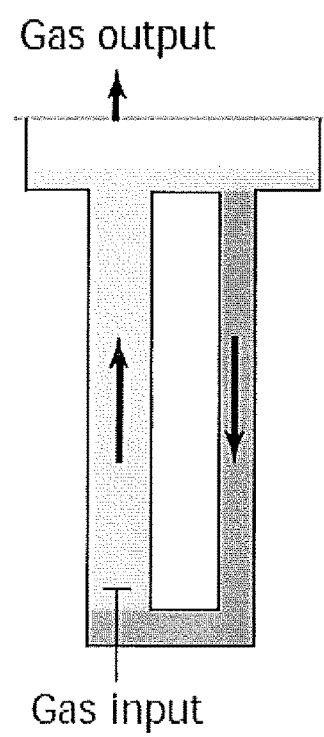
Figure 9:
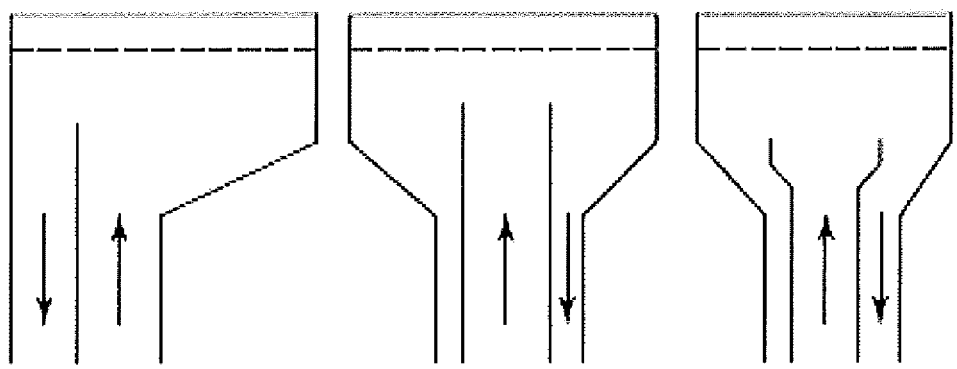
FIG. 9 illustrates six different gas separator configurations of internal-loop ALRs and three different gas separator configurations of external-loop ALRs for use in the present technology.
Figure 9:
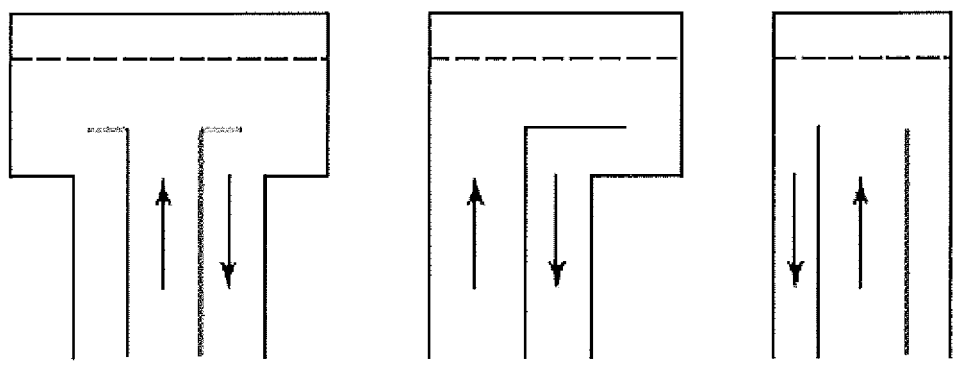
Figure 9:
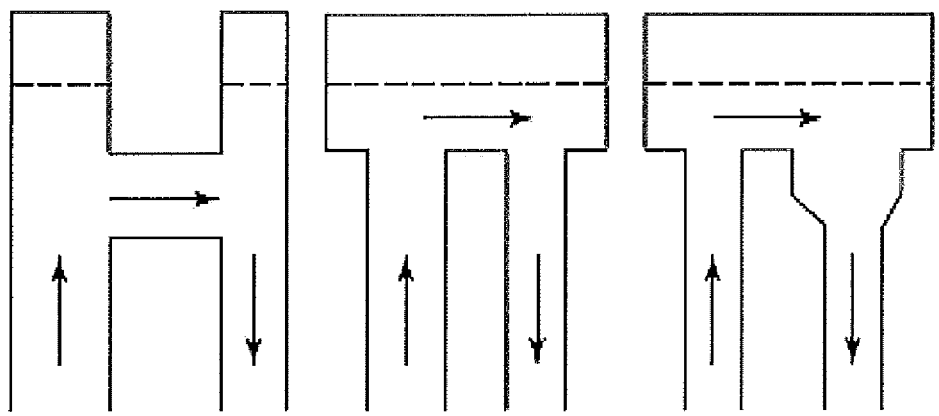

One or more of the bioreactor stages may also include an air-lift or bubble column system for mixing of biomass and aeration. Examples of a system for growing *Euglena* with an air lift is shown in FIG. 7 and examples of particular air lift reactors are shown in FIGS. 8 and 9. Air-lift reactors are known to provide adequate mixing and aeration with less shear stress on cells.

Figure 10:
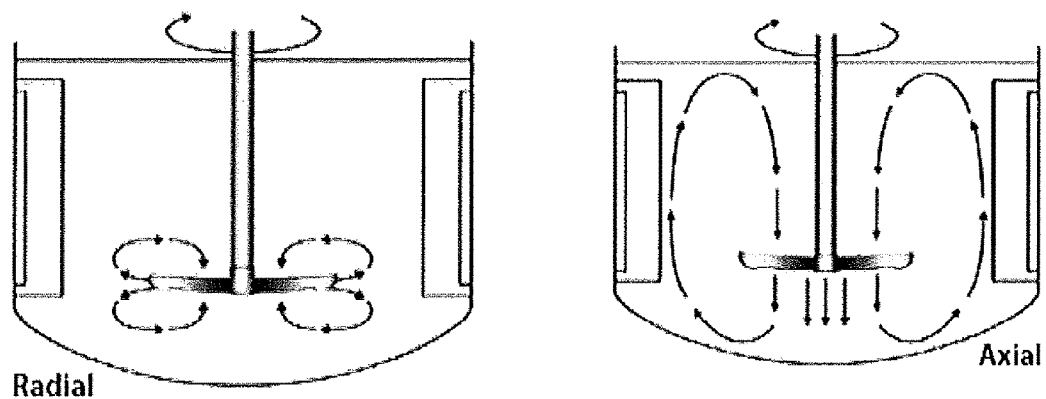
FIG. 10 illustrates mechanical agitation of *Euglena* growth media to produce radial mixing and axial mixing.
Figure 11:
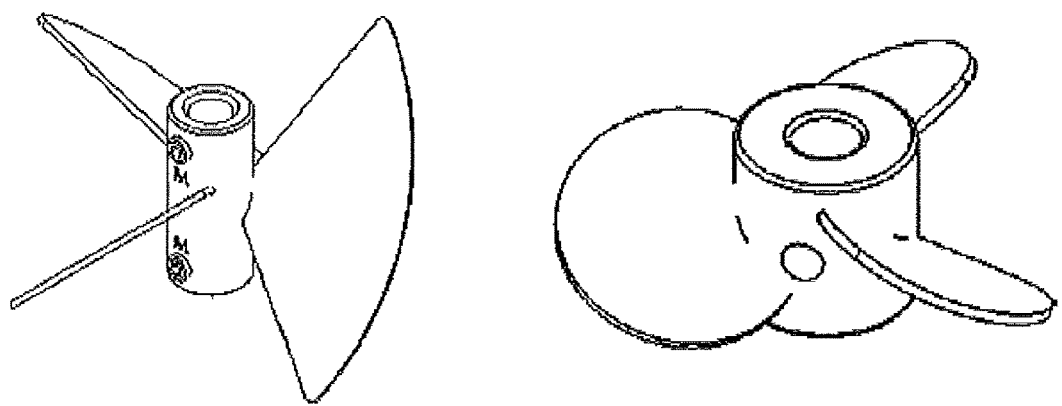
FIG. 11 illustrates two examples of low-shear blades for mechanical agitation of *Euglena* in growth media, including a fixed angle blade on the left and a marine blade on the right for use in the present technology.

Many industrial scale bioreactors however utilize a mechanical stirring apparatus for mixing and aerating the culture to provide radial and/or axial mixing as shown in FIG. 10. A mechanical mixing apparatus is suitable for mixing bacteria or yeast fermentations, including bacteria grown to produce recombinant proteins. Fermentation of yeast and bacteria currently make up the vast majority of industrial-scale fermentations. However, bacteria and yeast are smaller than *Euglena* cells, and are more shear tolerant. Certain types of mechanical stirring designs can be detrimental to the growth of *Euglena* cells and can even lyse the cells when used at high speeds. What is more, the *Euglena* cells grown using the present methods are swollen, partially due to the amount of paramylon that is stored within each cell. A mechanical stirring apparatus may destroy a large quantity of these cells and may not be preferable. In reactors where a mechanical agitator is present, a low-shear blade such as a marine blade or a fixed-angle blade is preferable. Examples of such low-shear blades are shown in FIG. 11.

Another version of the multistage bioreactor process is a repeated batch method for harvesting and/or transferring the biomass from the any bioreactor stage. This may also be referred to as operation in a repeated draw-and-fill mode. An example of a repeat batch harvest of *Euglena* growth versus time is shown in FIG. 12. Another example of a repeat batch method is shown in FIG. 22, where beta glucan, *Euglena* biomass density, timing of growth media removals and replenishments, and residual glucose in the growth media are shown. One or more batches can be harvested and/or transferred from one bioreactor stage each time it is inoculated by a previous bioreactor stage. A portion of the biomass can also be harvested and/or transferred from one bioreactor stage and another portion is left in the bioreactor stage. After this partial harvest and/or transfer, additional fresh growth media is added into the tank. The process can continue until either the desired amount of *Euglena* production is reached or until a contaminant organism eventually comprises a significant enough portion of the bioreactor to justify emptying the bioreactor and disinfecting it.

Another version of the multistage bioreactor growth method that is preferable is a continuous process that can maintain a certain amount of *Euglena* after an initial batch growth. FIG. 13 graphically depicts a batch phase followed by a continuous phase where *Euglena* culture is continuously harvested and replaced with fresh growth media. When used to produce *Euglena* with >30% beta-1,3-glucan, utilization of a continuous growth mode to produce *Euglena*, especially in the largest bioreactor in the train of bioreactors, can result in a highly economic level of production, Employment of a continuous process requires balancing the extraction rate with the input of crucial nutrients, as well as rapidly monitoring of levels of available energy, such as with an HPLC or with other spectrophotometric measures of monitoring carbohydrates. Incorporating a controls system with information feedback supplied by pH, dissolved oxygen, and other sensors is preferred in order to help ensure the continuous process remains balanced.

A repeat batch method according to the present technology can include the following aspects. *Euglena* is grown in a 50,000 liter bioreactor until the concentration of the *Euglena* reaches at least 20-60 grams per liter and the tank volume that is filled reaches 40,000 liters. Then 30,000 liters of the 40,000 liters are harvested. The tank is then gradually refilled with media, including the necessary carbon source and nutrients, and aerated and mixed until the tank is again filled to 40,000 liters with a *Euglena* concentration of 20-60 grams per liter.

After completing the multi-stage bioreactor stage the *Euglena* biomass is separated from the liquid component to reach at least 20% solids by use of a device such as a centrifuge, tangential flow filtration, filter press, belt press, or other solid-liquid separation device.

After this first dewatering process, an additional drying process is used to reach a solids concentration of at least 85% by use of a process such as a belt drier, spray drier, drum dryer, furnace or by spreading the biomass over a large surface area and using evaporative drying. Additional heat can be provided in this step. The drying process may also be carried out using a vacuum or partial vacuum environment (less than 1 atmosphere of pressure) in order to reduce the amount of time needed to dry the biomass product.

An additional process step may be included in order to separate the beta-1,3-glucan from the remaining biomass. Paramylon (*Euglena*-derived beta glucan) is a water insoluble beta glucan particle formed naturally by *Euglena* sp. as an energy storage compound. The paramylon granules are typically 0.5 to 2 micron in size and located within the *Euglena* cells. The paramylon granules can be extracted from the cells by simply lysing the cells and isolating the granules through either filtration or gravity separation (e.g., gravity settling, centrifugation). Lysing the cells can be achieved in a number of ways, including sonication, high pressure homogenization (e.g., French press), with or without the aid of chemicals and/or heating. Lysing can be aided by the addition of certain chemicals such as detergents (e.g., sodium dodecyl sulfate), enzymes or bases (e.g., sodium hydroxide) and acids (e.g., hydrochloric acid, acetic acid). The isolated paramylon granules can be further purified and washed of cell debris and lysing chemicals by washes with either water and/or alcohols. In one embodiment, the lysing process occurs in a separate tank after the biomass has been dewatered. In another embodiment, the lysing process can occur directly within the bioreactor. In addition to the methods described for cell lysing, *Euglena* cells can be induced to autolyse given certain environmental conditions.

A preferred method for extraction is to heat the *Euglena* cells in a 1% sodium dodecyl sulfate solution, centrifuge the solution, and wash the pellet with water and ethanol. At the lab scale, the paramylon extraction process can be achieved in the following way. Approximately one part *Euglena* biomass (dry weight basis) is suspended in 5 parts of 1% (w/v) sodium dodecyl sulfate solution. This solution mixed vigorously and then heated to 100° C. for 30 minutes. The solution is then cooled and centrifuged at >500 RCF for 5 minutes. The supernatant is discarded and the pellet is washed by re-suspension in 10 parts water, mixed vigorously and centrifuged at >500 RCF for 5 minutes. The washing process can be repeated two more times with 10 parts 95% ethanol, to arrive at a 95% pure beta glucan pellet. The pellet can be further dried to a white/tan powder.

These methods can result in beta glucan purity levels greater than 99% when combined with highly beta glucan rich *Euglena* grown using a *Euglena* growth process according to the present technology. The methods described here are also less toxic than some of the previous methods described for extracting paramylon, which may have added benefit of receiving safety and all-natural product certifications necessary for producing a food-grade or nutraceutical-grade product. Commonly extracted yeast-based products typically have purity levels of no greater than 80% beta glucan on a dry weight basis in various commercial products. Although other multi-stage growth techniques have been described that can result in paramylon concentrations of 95% to 97% purity (e.g., U.S. Pat. No. 5,084,386), such techniques are not feasible at a commercial scale and involve hazardous solvents (e.g. methanol and chloroform). The increased beta-1,3-glucan purity levels are valuable in immune-stimulating products that require higher levels of purity, such as applications for humans and injectable beta glucan products, such as for vaccine adjuvants. Higher purity levels of beta-1,3-glucan are also useful when the extracted paramylon is used as a precursor or base carbohydrate unit for additional processing steps that increase the biological binding affinity, solubility, or other desired biological properties of the beta glucan compound, such as additional amination or sulfation steps that are further described herein.

Extracted paramylon from the processes described herein may undergo additional process steps in order to increase the binding affinity to immune system receptors, such as Dectin-1, a protein that has been identified as a beta glucan receptor. For example, sulfated polysaccharides have been demonstrated to display anti-HIV activity (e.g., U.S. Pat. No. 5,861,383). Sulfated derivatives of paramylon may also be shown to display anti-HIV activity. One method for preparing sodium paramylon sulfate is to dissolve the paramylon in dimethyl sulfoxide, to add into this a mixture of dry pyridine and chlorosulfonic acid, to heat the reaction mixture, and to decant the supernatant. Following this, distilled water and methanol may be added in order to precipitate pyridinium paramylon sulfate, which can then be collected by filtration, Adding NaCl solution and raising pH to 9 may then precipitate sodium paramylon sulfate in an acetone solution (Sakagami et al; In vivo 3:243-248 (1989)). This process step may occur in the same facility or in fluid communication with the previously described multistage process, although it may also occur in a different facility after the dried *Euglena* is shipped. This process may also be performed without undergoing the previously described liquids-solids separation or drying process stages, although these stages may be deployed. In some cases, this stage may also be carried out in the last bioreactor vessel.

Paramylon produced in the previously described multi-stage process can be more biologically active as an immunomodulator when it receives additional processing in order to make it positively charged (Sakagami et al.; *Antiviral Research*, 21:1-14 (1993)). The DMAE-paramylon may be more effective as it may cause increased binding affinity with beta-1,3-glucan receptors, such as Dectin-1 and complement receptor 3. However, several different processes may be used in order to positively charge the paramylon produced in the multistage process for production of paramylon from *Euglena* to be used in immunomodulatory applications. However, one process for producing positively charged paramylon may be to react the paramylon with N,N-dimethylaminoehyl (DMAE). In this process, paramylon may be dissolved into a base solution, such as one that may be prepared through the addition of NaOH. DMAE-chloride hydrochloride solution may be added in the form of a solution as a dry powder in order for the reaction to occur. This process may be performed in the same facility or in a separate facility. Also, it may be performed on an extracted paramylon product produced using the multistage bioreactor processes described herein. Alternatively, this process may be performed in a single step in order to simultaneously separate the paramylon from the *Euglena* biomass and to react it with DMAE in order to make it positively charged for increased immunostimulant activity. By performing the paramylon extraction from biomass and DMAE activation in a single step, the cost of DMAE-activated paramylon, and the net cost per dose, can be reduced by a factor of ten.

Growing *Euglena* according to the present technology can further include the following aspects. Growth media for *Euglena* can include: potassium phosphate from 0.25 to 5 g/L; magnesium sulfate from 0.25 to 5 g/L; calcium chloride from 0.005 to 0.5 g/L; and a trace metal stock solution containing several micronutrients (e.g., Fe and Zn), each at 0.1 to 500 mg/L. Optionally, a buffer can be included in the media to help reduce the requirement of pH control chemicals. Dextrose can be supplied in the initial growth media as well as semi-continuously or continuously throughout cultivation such that its concentration is between 0.5 and 30 g/L.

As the primary nitrogen source, ammonium hydroxide is used, where ammonia gas can be provided into the aqueous media to form ammonium hydroxide. This is in contrast to other *Euglena* growth media that use ammonium salts (e.g., ammonium sulfate) and amino acids like glutamate as the primary nitrogen source. Low levels of ammonium sulfate (0.1-2 g/L) can be used in the *Euglena* growth media, especially during flask-scale or small scale cultivation, but the majority of nitrogen in the biomass is derived from ammonium hydroxide or ammonia gas at production scale. Growth temperature can be 30 degrees C. to 32 degrees C. The pH of the growth media can be 3.0 to 3.5. Oxygen levels can be maintained at 0.5 mg/L to about 4 mg/L, where in one embodiment the oxygen is maintained at 2 mg/L (i.e., 15-30% saturation). The growth media can also include one or more antifoaming agents.

*Euglena* batches can be scaled up as follows. A 50 ml culture of *Euglena* can be used to inoculate 1 liter of growth media, where the 1 liter culture can be used to inoculate a 10 liters of growth media, where the 10 liter culture can be used to inoculate 400 liters of growth media, where the 400 liter culture can be used to inoculate 10,000 liters or 38,000 liters of growth media. Optionally, an intermediate growth step can be used between the 400 liter and 10,000 liter steps, and optionally a larger growth step can be performed after the 10,000 liter or 38,000 liter step (e.g., a 250,000 liter step). The 50 ml and 1 liter cultures can be incubated on a shaker, the 10 liter culture can be incubated in a stirred bioreactor, and the 400 liter, 10,000 liter, and 38,000 liter cultures can be incubated in an airlift or bubble column reactor. The 400 liter, 10,000 liter, and 38,000 liter cultures can be maintained in a continuous or repeat batch fashion where a portion of the culture is removed and replaced with fresh growth media in a continuous process or in batches, respectively. This could also be described as a repeated draw and fill operation. The continuous or repeat harvests of *Euglena* cultures can be continued for days or weeks as long as the amount of any contaminating microorganisms (e.g., yeast, bacteria) is sufficiently suppressed. The *Euglena* batches can use *Euglena gracilis* strain Z.

The *Euglena* can be grown to a density of at least 20-60 g/L, where the culture can be maintained at or near this density in a continuous fashion or a portion harvested and the residual culture replenished with fresh media and regrown to this density in one or more repeated batches. In certain embodiments, the *Euglena* culture can be grown to a density of at least 80-120 g/L. The *Euglena* cell division rate using the present technology can be about 24 hours or faster. Harvested *Euglena* culture can provide an output of at least about 20 g of *Euglena* biomass per liter of culture per day when averaged over the course of many successive runs.

*Euglena* grown according to the present methods typically have greater than 30% beta glucan and typically less than 70% beta glucan (i.e., 30%<beta glucan<70%). In certain embodiments, the *Euglena* have 35%<beta glucan<65%. In other embodiments, the *Euglena* have 40%<beta glucan<60%. The beta glucan content of the *Euglena* can be affected by the growth media, fermentation temperature, and growth time, However, unlike other methods used to grown *Euglena*, the present technology is not directed at maximizing the beta glucan content of the *Euglena*, where other methods have grown *Euglena* to greater than 70% beta glucan, including 70%<beta glucan<90%. Where the *Euglena* growth is not deliberately directed to maximizing beta glucan production, a greater portion of the carbon source in the media can be converted into other components of the *Euglena* biomass. Without being bound by theory, it is believed that other components of the *Euglena* biomass can act alone, in concert, or in a synergistic fashion with the beta glucan to provide an immunomodulatory function in animals, including humans. Supporting data are presented herein.

The growth methods, systems, and compositions used in the present technology can include certain variations and additional aspects. In some embodiments, a multi-stage method for the cultivation of *Euglena* is provided that includes growing *Euglena* in a first bioreactor stage. The *Euglena* are then grown in a second bioreactor stage that is inoculated from the first bioreactor stage, where the second bioreactor stage has a greater volume than the first bioreactor stage. The *Euglena* can be further grown in a third bioreactor stage that is inoculated from the second bioreactor stage, where the third bioreactor stage has a greater volume than the second bioreactor stage. Liquid can be separated from the *Euglena* following the third bioreactor stage.

As described, the *Euglena* can be *Euglena gracilis* strain Z. However, the *Euglena* can be any species of the genus *Euglena*, including *Euglena* strains that demonstrate reduced chlorophyll production or lack chloroplasts as a result of natural selective pressures or mutation. Aspects of the present technology include growing the *Euglena* in ways that prevent any phototrophic growth; e.g., all cultures can be maintained in the dark. The methods and systems can be configured so that *Euglena* growth is carried out in predominantly dark conditions so that greater than 95% of the energy provided for growth of the *Euglena* is in the form of dissolved organic carbon sources rather than from light. The *Euglena* cell doubling time can be maintained in a range of one division occurring between 6 hours and 24 hours. *Euglena* can be grown in this fashion to densities greater than 20-60 grams per liter.

Variations of the growth media include the following. The pH of the growth media in one or more of the various bioreactor stages can be maintained at a range between 2 and 6 through use of a buffer system. Any suitable buffer capable of maintaining pH within the range of 2 to 6 may be used. The pH in at least one of the growing steps can be maintained using an automated control system in fluid communication with at least one of the bioreactor stages that is configured to add acid, base, or a buffer in order to reach a target pH. The growth media can also include a complex source of concentrated vitamins, proteins, and nutrients such as corn steep liquor, yeast extract, or peptone. One or more of nitrogen, iron, magnesium, and phosphorus elements can be added to a bioreactor stage in the form of a salt or a media solution to provide the concentration levels described herein. In a certain aspect, less than 2 g of an organic carbon source is added for every 1 g of biomass that is harvested from a final bioreactor stage.

Certain aspects of growing *Euglena* can be automated. For example, at least one of the bioreactor stages can have growth media added using a programmable control system and sensors in electronic communication with a programmable control system configured to add one or more media components in response to the detection of one or more process parameters. Variables detected by the sensors can include one or more of dissolved oxygen in the growth media, pH, pressure, glucose concentration, organic acid concentration, cell density or turbidity, phosphorous, nitrogen, dissolved carbon dioxide, carbon dioxide concentration in the exhaust gas or oxygen concentration in the exhaust gas. One or more of the bioreactors can automatically control the temperature so that it is maintained between twenty and thirty-five degrees Celsius. Likewise, the dissolved oxygen level can be maintained between 5 percent and 90 percent of saturation levels.

Various bioreactors can be employed. The bioreactors can be made of glass, plastic, or stainless steel. When glass or plastic is used, the bioreactor can be opaque to prevent phototrophic growth of the *Euglena* and maintain heterotrophic growth conditions. The various bioreactors can be sterilized between batches using steam, ethanol, pressure, UV, a disinfectant, or a combination thereof. The bioreactor can be designed to withstand internal pressure of at least 15 PSI when pressured steam sterilization is used. The bioreactor tank can also be sterilized using a concentrated ethanol solution. In certain aspects, at least a portion of the ethanol solution can be left in the bioreactor to be utilized as a carbon source by the *Euglena*.

At least one of the bioreactors used in the methods and systems described herein can be in fluid communication with one or more tanks containing the growth media or growth media components as described. Fluid communication between the various bioreactors and the growth media can be separated by one or more sterile filters (e.g., pore size less than about 0.2 microns) to prevent unwanted microorganisms from entering the bioreactor tank. The bioreactor can include a mechanical stirring mechanism or the bioreactor can include an airlift apparatus for mixing the *Euglena* and growth media within the bioreactor. The mechanical stirring mechanism can be configured to provide shear stress that is less than the shear required to lyse *Euglena* cells.

In scaling up *Euglena* cultures and/or maintaining *Euglena* cultures, the following aspects can be used. A concentration of *Euglena* in a bioreactor immediately following inoculation can be less than 10 grams per liter. A harvest concentration of *Euglena* can be greater than 20-60 grams per liter, and can be greater than 80-120 grams per liter in some cases. A volume of a successive bioreactor stage can be between about 5 times and about 200 times greater than a previous bioreactor stage. One of the bioreactor stages can be between 10 liters and 250 liters in volume and can employ a reactor such as a New Brunswick BioFlo 3000 or 4500 bioreactor.

In a certain aspect, fresh growth media can be continuously added to a *Euglena* culture while a portion of the *Euglena* culture is continuously harvested. The fresh growth media can be complete media or can include individual components, mixtures of components, stock concentrated solutions of components, solid, pelletized, or powdered components, water, etc. Some methods and systems may only use one reactor where fresh growth media is added on a continuous basis. For example, *Euglena* can be grown in a batch fashion in a first stage bioreactor and/or a second stage bioreactor to inoculate a later stage bioreactor, where the later stage bioreactor includes a larger culture volume that is continuously replenished with fresh growth media while being *Euglena* culture is continuously harvested. An example includes where the concentration of *Euglena* in a bioreactor is greater than 20 grams per liter when a continuous harvesting phase is initiated, and where the concentration of *Euglena* is maintained at greater than 20 grams per liter during the continuous harvesting phase.

Other aspects include where at least one bioreactor stage is operated in a batch mode; i.e., where anywhere from a portion to substantially the entire *Euglena* culture is harvested or used to inoculate another bioreactor. The batch mode can be repeated so that the bioreactor is operated in a repeat batch mode; i.e., where a portion of the *Euglena* culture is harvested and replaced with a portion of fresh growth media and growth is continued. In certain embodiments, the repeat batch mode consists of removing between 99.5% to 10% of the volume of *Euglena* culture within the bioreactor and refilling the tank with usually a like amount of sterilized growth media. The repeat batch mode can be done many times. Contamination of undesired microorganisms can be monitored to determine when the repeat batch mode should be terminated and the contaminated batch discarded.

Harvested *Euglena* can be separated from growth media using any number of solid-liquid separation techniques. Examples of solid-liquid separation techniques include centrifugation, filtration, use of a belt press, spray drier, belt drier, and the like. The separated *Euglena* can be prepared as a powder, granulate, pressed into pellets, or extruded in various forms. These various forms can be referred to generically as algae meal.

In some aspects, paramylon (i.e., beta glucan) can be extracted from the *Euglena*. For example, continuously harvested *Euglena* or the sum of repeat batch harvests can be collected and simultaneously extracted or the repeat batch harvests can be extracted in separate batches. The paramylon concentration at harvest can make up greater than 40% of the total biomass harvested, as measured by dry weight. The paramylon extraction process can include a cell-lysing step followed by a step where the paramylon is solubilized in an extraction solution and a further step where the solubilized paramylon is precipitated out of the extraction solution. Certain embodiments lyse the *Euglena* cells using sodium dodecyl sulfate or another detergent. Other methods include lysing the *Euglena* cells using a physical process such as mechanical agitation, high pressure homogenization, direct heat, or microwaving. In some cases, the *Euglena* cells are lysed using internal or external cell pressure resulting from an osmotic gradient between the internal contents of the cell and the surrounding media. The paramylon can then be separated from the *Euglena* cell debris by a process that utilizes the greater density of the paramylon molecule, such as by allowing the paramylon to settle to the bottom of a cone-shaped tank or by using a centrifuge step. The lysing step can be coupled with the solid-liquid separation, such as where the *Euglena* cells are lysed in the final bioreactor tank prior to a dewatering step, such as centrifuging or drying. Extracted paramylon can have a concentration of beta glucan greater than 90% on a dry weight basis.

The algae meal or the extracted paramylon produced using the present methods, system, and compositions demonstrates surprising and unique properties with respect to modulating the immune function of an animal, including a human. In particular, the beta glucan present in *Euglena* provides a surprising and unique effect in modulating the immune function of an animal while the remainder of the *Euglena* cell mass in the algae meal further provides an effect that acts in concert or synergistically with the beta glucan. These effects can be observed by administering the algae meal at a daily dose of between 0.0001% and 0.1% of the total weight of the animal. In certain aspects, the beta glucan in the algae meal can be modified to include an amine functional group, phosphate group, and/or a sulfate group. In certain aspects, modified beta glucan can be added to the algae meal containing unmodified beta glucan.

Example analyses of algae meal produced according to the present technology are provided below as Tables 1 and 2.

TABLE 1

Algae Meal Analysis

| Assay | Reporting limit | Units | Batch 1 As Received | Batch 1 Dry Weight | Batch 2 As Received | Batch 2 Dry Weight |
|---|---|---|---|---|---|---|
| Moisture | 0.01 | % | 7.92 | | 6.53 | |
| Dry Matter | 0.01 | % | 92.08 | | 93.47 | |
| Beta-1,3-glucan | 0.1 | % | 46.0 | 50.0 | 45.7 | 48.9 |
| Protein (crude) | 0.2 | % | 33.0 | 35.8 | 32.7 | 35.0 |
| Fat (crude) | 0.1 | % | 3.17 | 3.44 | 3.46 | 3.70 |
| Sulfur (total) | 0.01 | % | 0.41 | 0.45 | 0.44 | 0.47 |
| Phosphorus (total) | 0.01 | % | 1.27 | 1.38 | 1.18 | 1.26 |
| Potassium (total) | 0.01 | % | 0.46 | 0.50 | 0.42 | 0.45 |
| Magnesium (total) | 0.01 | % | 0.14 | 0.15 | 0.11 | 0.12 |
| Calcium (total) | 0.01 | % | 0.02 | 0.02 | 0.02 | 0.02 |
| Sodium (total) | 0.01 | % | 0.08 | 0.09 | 0.08 | 0.09 |
| Iron (total) | 5 | ppm | 227 | 247 | 213 | 228 |
| Manganese (total) | 1 | ppm | 19.2 | 20.9 | 16.1 | 17.2 |
| Copper (total) | 1 | ppm | 14.4 | 15.6 | 13.9 | 14.9 |
| Zinc (total) | 1 | ppm | 72.7 | 79.0 | 65.5 | 70.1 |
| E. coli (generic) | 10 | cfu/g | n.d. | | n.d. | |
| Total coliforms | 10 | cfu/g | n.d. | | n.d. | |
| Staphylococcus aureus | 10 | cfu/g | n.d. | | n.d. | |
| Salmonella | 1 | org/25 g | negative | | negative | |
| Arsenic (total) | 10.00 | ppm | n.d. | | n.d. | |
| Lead (total) | 5.00 | ppm | n.d. | | n.d. | |
| Cadmium (total) | 0.50 | ppm | n.d. | | n.d. | |
| Antimony (total) | 5.00 | ppm | n.d. | | n.d. | |
| Mercury (total) | 0.05 | ppm | n.d. | | n.d. | |

TABLE 2

Algae Meal Specialized Analyses on Single Batch

| Assay | Value |
|---|---|
| Vitamin C (mg/100 g) | 10.2 |
| Vitamin E (IU/kg) as alpha tocopherol | 34 |
| Omega 3s (% of dry weight) | 0.78 |
| Omega 6s (% of dry weight) | 0.82 |
| Docosahexaenoic DHA % of dry weight | 0.22 |
| Eicosapentaenoic EPA % of dry weight | 0.33 |
| Total Aflatoxins (including B1, B2, G1, G2) (ppb) | <1 |
| DON (Vomitoxin) ppm | <0.1 |
| Total fumonisin (including B1, B2, B3) ppm | <0.1 |
| Ochratoxin (ppb) | <1 |
| T-2 Toxin (ppm) | <0.1 |
| Zearalenone (ppb) | <50 |
| Mold count (cfu/g) | <10 |
| Yeast (cfu/g) | <10 |
| Salmonella (org/25 g) | negative |
| E. coli (cfu/g) | <10 |
| Aerobic plate count (cfu/g) | <10,000 |
| Total coliforms (cfu/g) | <20 |
| Staphylococcus aureus (cfu/g) | <10 |
| Other algae-specific toxins: | |
| microcystin, euglenophycin, cylindrospermopsin, saxitoxin, brevetoxin, diarrheic shellfish poisonin, and amnesiatic shell fish poisoning | Negative |
| Other algae-specific carotenoids: | |
| lutein (ng/g d.w.) | 145,707 |
| zeaxanthin (ng/g d.w.) | 2,895 |
| astaxanthin (ng/g d.w.) | 7,597 |
| beta-carotene (ng/g d.w.) | 59,353 |
| carotenoid-related breakdown products (ng/g d.w.) | 205,444 |

Harvested algae meal and extracted paramylon (i.e., beta glucan) prepared according to the present technology were investigated to ascertain their abilities to modulate the immune system of animals.

The primary objectives of these experiments were to:
1) Determine whether algae meal and beta glucan extracted from *Euglena* stimulated the immune system of mice when dosed orally by measuring antibody production, natural killer (NK) cell cytotoxicity, and phagocytosis activity.
2) Compare the effects of algae meal and beta glucan extracted from *Euglena* to yeast-derived beta glucan products currently used as animal feed supplements.
3) Evaluate the effectiveness of algae meal (containing about 50% beta glucan) to purified algae beta glucan (>90% pure).

Methods:

Algae cells were grown in a sterile fermenter as described. Two algae meal biomass samples, labeled WBG50A and WBG50B, were used in a mouse study. The WBG50A biomass sample was produced using glucose as the organic carbon source, while biomass for the WBG50B sample was produced using ethanol. Once the target density of biomass was reached in the fermenter, the cells were centrifuged and the resulting paste was stored frozen at −20° C. To produce the algae meal sample, the frozen paste was thawed, dried at 65° C. until it formed a dry flake, and then ground to a particle size of less than 1000 microns to less than 500 microns. The centrifuged algae meal paste could optionally be dried immediately instead of frozen for storage. The purified beta glucan sample was produced by fractionating the algae cells and isolating the beta glucan to produce >90% beta glucan having a particle size of less than 500 microns. Two yeast-derived beta glucan (YDBG) products, named YDBG-1 and YDBG-2, were procured from a commercial distributer and used without further modification, Each of the dry products was mixed with phosphate buffered saline (PBS) and diluted to appropriate concentrations before being dosed by gavage to mice at the prescribed dosing levels.

Three BALB/c mice were allocated to each treatment and given varying levels of beta glucan on a weight percent of their total diet basis ranging from less than 0.001% to 0.25% of the mouse diet ration. For clarity, only the data from the 0.0035% and 0.035% dosing levels are represented in FIGS. 14-17.

Blood was taken from each mouse to measure non-specific immune system activity. The following parameters were assessed 48 hours after a single feeding of each beta glucan product: phagocytosis activity (the ability of macrophages to ingest foreign particles), natural killer (NK) cell activity (the ability of NK cells to destroy foreign or infected cells), and cytokine concentrations (IL-2). To measure the capacity of the specific immune response, antibody formation in response to ovalbumin was measured via an enzyme-linked immunosorbent assay (ELISA) using a Freund adjuvant as a positive control and PBS as the negative control. Mice were injected with ovalbumin on day 0 and 14 and fed a specified dose of each beta glucan product once per day from day 0 to day 14. Antibody titers were measured on day 21.

All animal work was conducted in the laboratory of Dr. Vaclav Vetvicka in the Department of Pathology at the University of Louisville. Dr. Vetvicka is well known for his research on the physiological effects of beta glucan and his lab has conducted numerous side-by-side comparisons of beta glucan products in the marketplace to determine their potential effectiveness.

E, coli Bacteria Challenge: Ten BALB/c mice were allocated to each treatment group and received a nominal lethal dose of *E. coli* (3×10$^7$) via intramuscular injection on day 0. Beta glucan products (0.01% of the daily feed ration by weight) were orally dosed by gavage to the mice daily starting two days prior to the *E. coli* injection (day −2) through two days following the injection (day +2). The control group received only a PBS gavage, while an antibiotic-treated group received oral doses of Ampicillin (13 mg/kg) on days 0, 1, 2, 3 and 4. Mice were evaluated daily up through day 10.

Antibody Titers: Three BALB/c mice were allocated to each treatment group and received a daily oral dose of beta glucan products equivalent to 0.002, 0.005, 0.010 and 0.020% of their daily feed ration by weight starting on day 0. The antigen (ovalbumin) was given by intraperitoneal injection on days 3 and 16 and antibody titers were measured on day 23 using an ELISA assay with a PBS gavage as the negative control.

NK Cell Cytotoxicity and Phagocytosis Activity: Nine BALM mice were allocated to each treatment group and fed beta glucan products in the same manner as the antibody titer experiment explained above in order to measure natural killer (NK) cell cytotoxicity (the ability of NK cells to destroy foreign or infected cells) and phagocytosis activity (the ability of macrophages to ingest foreign particles). On days 1, 7 and 14, three mice from each treatment group were sacrificed to harvest material for analyses. NK cell activity (measured as cytotoxicity) is an index of the ability for isolated NK cells from the spleen to kill target cells (e.g., YAC-1 cells from a T-lymphoma cell line) during a 4 hour incubation. The phagocytosis index is measured as the percent of neutrophil cells that actively capture and engulf labeled particles in an allotted time.

Results:

Phagocytosis is one response by the immune system to capture and destroy potentially harmful particles or organisms. The phagocytosis index is measured as the percent of neutrophil cells that actively captured and engulfed labeled particles. Mice that were given only the PBS control had a phagocytosis index of 30% (FIG. 14). The highest recorded index (45%) was observed for mice fed the 0.035% dose of WBG50B, which is a 50% increase over the control treatment. Overall, the WBG50B treatment had the highest phagocytosis index of all the treatments at each of the two dosage levels and was especially effective compared to all of the treatments at the lowest dosage level (0.0035% of diet).

NK Cell Activity is an index of the ability for isolated natural killer (NK) cells from the spleen to kill target cells (e.g. YAC-1 cells from a T-lymphoma cell line) during a 4 hour incubation. Mice that were fed the PBS control displayed a cytoxicity index of 12%, while the mice fed the 0.035% dose of WBG50B had a cytoxicity index over three times higher (38.5%)(FIG. 15). Both the WB50B and the extract treatments substantially outperformed the yeast-derived beta glucan products at both dosage levels and in some cases, the WBG50B treatment showed nearly twice the cytotoxicity of YDBG-2 at both the 0.035% and 0.005% dosage levels.

Interleukin-2 (IL-2) is an important cytokine messaging molecule that helps regulate the immune response to microbial infection. IL-2 production is measured as the amount of IL-2 produced by harvested spleen cells during an incubation period. IL-2 response is a more generalized immune response than NK cell activity, phagocytosis and antibody formation. As such, many different types of foreign compounds, not just beta glucan, can elicit an increase in IL-2 production. Mice that were fed the PBS control did not observe an increase in IL-2 production, while all of the beta glucan product treatments elicited a very strong IL-2 response that was noticeably increased at the higher dosage rate (FIG. 16). The algae beta glucan extract treatment resulted in the highest IL-2 production, followed by the yeast-derived beta glucan products and then the WBG50 products.

Antibody Formation indicates the potential for a beta glucan to serve as an adjuvant (enhancer) to vaccines. In this case, mice were injected with ovalbumin, then fed beta glucan products daily for 14 days, and then antibodies to ovalbumin were measured in the serum. Freund adjuvant (an emulsion of inactivated bacteria cells) was used as a positive control as it is recognized as an industry standard for inducing antibody formation. However, Freund adjuvant is not used in many animals including humans because of its strong toxicity effect. As expected, the Freund adjuvant produced a very high level of antibodies (FIG. 17). The WBG50B and algae beta glucan extract treatments also demonstrated high antibody formation, especially at the highest dosage level (0.035% of diet). The yeast-derived beta glucan products induced roughly half the antibody response as the WBG50B and algae beta glucan extract treatments at the 0.035% dosage rate.

*E. coli* Bacteria Challenge (FIG. 18): All mice in the control group, which received only PBS, died within seven days of the *E. coli* injection. In contrast, mortality at day 10 was decreased in all treatment groups by at least 40%. Notably, 70% of the mice receiving purified algae beta glucan product survived 10 days following *E. coli* injection. This treatment group and the one receiving Ampicillin showed very similar survival rates over time, suggesting that the algae-derived beta glucan treatment provided similar protection against bacterial infection as the common antibiotic Ampicillin. Mice receiving algae meal, which contains about 50% beta glucan, also showed a significant decline in mortality compared to the control group. In this treatment group, 50% of the mice survived 10 days following *E. coli* injection compared to 40% surviving in the group fed a yeast-derived beta glucan extract.

Antibody Titers (FIG. 19): Significant increases in antibody titers indicate the potential for products like beta glucan to serve as an adjuvant (enhancer) to vaccines. All of the beta glucan treatment groups elicited an increase in antibody production relative to the negative control and this effect was enhanced at higher doses. The purified algae beta glucan treatment produced the most antibodies at each of the treatment levels followed closely by the algae meal treatment group. The mice fed the yeast-derived beta glucan product demonstrated substantially lower (between 15 and 50% lower) antibody titers compared to those fed the purified algae beta glucan and algae meal at moderate dosing levels (0.005 and 0.010%) but had similar titers to mice fed the algae meal treatment at the highest dosage rate.

NK Cell Cytotoxicity (FIG. 20): NK cell cytotoxicity is an index of the non-specific immune response by NK cells to kill potentially pathogenic organisms. Mice that were fed the PBS control displayed a cytotoxicity index of 12%, while the mice fed with doses as low as 0.005% of either the algae meal or purified algae beta glucan demonstrated a cytotoxicity index over three times higher (36 to 50%). At doses of 0.005% and higher, both the algae meal and purified algae beta glucan treatments elicited a stronger cytotoxicity response than the yeast-derived beta glucan product.

Phagocytosis Activity (FIG. 21): Phagocytosis is another non-specific immune response to engulf potentially pathogenic organisms. Mice that were given only the PBS control had a phagocytosis index of 30% while mice fed the highest dose of the purified algae beta glucan demonstrated nearly twice the phagocytosis activity (59%). As seen with the NK cell cytotoxicity and antibody titers, the purified algae beta glucan treatment group demonstrated the best performance at each dosage level. The mice fed algae meal and yeast-derived beta glucan demonstrated similar phagocytosis activity at the two lowest dosage levels, but mice fed yeast-derived beta glucan at the two highest dosage levels had slightly higher phagocytosis activity.

CONCLUSIONS

1) Each of the Algal Scientific beta glucan products (WBG50A, WBG50B, algae beta glucan) induced significant increases in each the immune responses measured (phagocytosis, NK cell activity, IL-2 production, antibody production) compared to controls. In particular, WBG50B (biomass grown on ethanol as the carbon source), demonstrated the highest measured levels for three of the four immunity indexes (phagocytosis, NK cell activity and antibody formation).
2) For each measure of immune response, Algal Scientific's beta glucan products performed as well and in many cases better than yeast-derived beta glucan products on the market today. Notably, the immune response in NK cell activity and phagocytosis for the lowest dose of WBG50B was greater than the response to the highest dose of the yeast-derived beta glucan products, suggesting the possibility for reduced dosing requirements for Algal Scientific's products.
3) In most cases, the immune response to algae meal or whole cell biomass (e.g. WBG50B) was as high, if not higher, than the extracted beta glucan alone. This suggests that other components of the algae cells (e.g., omega-3 fatty acids, vitamin E, trace metals) may act complementary to the beta glucan to induce a stronger immune response. In addition, it suggests that the cell is readily digestible and that the beta glucan is bioavailable.
4) In all cases, the immune response to the two dosage levels (0.0035% and 0.035%) was not linear (i.e. 10× higher) and differed among products, suggesting that the optimal dosage rate for the beta glucan products is likely much lower than the highest dosage level (0.035%). Additionally, dosage rates could be optimized for phagocytosis response, which is the first line of defense against pathogens.
5) Each of the beta glucan products (Algal Scientific's algae meal, Algal Scientific's purified algae beta glucan, and the yeast-derived beta glucan) increased the survivorship of mice exposed to a lethal dose of *E. coli*. In particular, the algae meal treatment increased survivorship at day 10 from 0% in the control group up to 50%. The purified algae beta glucan treatment increased survivorship up to 70%, which was the same response as the antibiotic treatment (Ampicillin). These data suggest that algae-derived beta glucan has potent antibacterial activity and that beta glucan within the algae meal, which has not been extracted and purified, is readily bioavailable.
6) Both specific immune responses (i.e., antibody production) and non-specific immune responses (NK cell cytotoxicity and phagocytosis activity) increased significantly for treatment groups fed any of the beta glucan products. For all of the immune metrics, purified algae beta glucan treatment group elicited the strongest immune response at all treatment levels.
7) Both Algal Scientific's algae meal and purified algae beta glucan products elicited a very strong antibody response that was several fold higher than the titers found in the negative control. These data indicate the potential for these products to serve as adjuvants.
8) Algal Scientific's algae meal product performed as well if not better than the yeast-derived beta glucan product at nearly all treatment levels in both antibody production and NK cell cytotoxicity assays. In most cases, the algae meal product induced nearly the same or better response compared to the yeast-derived product at only a quarter to half the dosage level.
9) The yeast-derived beta glucan product elicited a lower phagocytosis response than the purified algae beta glucan product but performed as well or better than the algae meal product in this category. In general, the overall impact of all beta glucan products on phagocytosis is more tempered than NK cell cytotoxicity and antibody production.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions and methods can be made within the scope of the present technology, with substantially similar results.

What is claimed is:
1. A method for growing *Euglena* comprising:
   (a) growing *Euglena* heterotrophically in a growth media in a vessel to form a culture, wherein the *Euglena* are grown to a concentration of at least 50 grams dry weight per liter and the *Euglena* have greater than 30% by weight beta glucan and less than 70% by weight beta glucan;
   (b) removing a portion of the culture from the vessel to form a removed portion; and
   (c) replenishing the remaining culture in the vessel with fresh growth media to form a replenished culture;
   wherein the productivity of *Euglena* grown by steps (a), (b), and (c) is at least 20 grams dry weight per liter of culture maintained in the vessel per day, and
   wherein a carbon source in the growth media in steps (a) and (c) is less than 30 grams per liter.
2. The method of claim 1, wherein the *Euglena* in the culture of step (a) have greater than 40% by weight beta glucan and less than 60% by weight beta glucan.
3. The method of claim 1, further comprising growing *Euglena* in the replenished culture of step (c) to a concentration of at least 50 grams dry weight per liter.
4. The method of claim 3, further comprising:
   (d) removing a portion of the replenished culture from the vessel to form a removed replenished portion.
5. The method of claim 4, further comprising:
   (e) replenishing the remaining culture in the vessel with fresh growth media.
6. The method of claim 4, further comprising combining the removed portions of steps (b) and (d).

7. The method of claim 6, further comprising one of:
separating the combined removed portions into a solid portion comprising the *Euglena* and a liquid portion, and drying the solid portion to form an algae biomass; and
extracting the combined removed portions to isolate paramylon from the *Euglena*.

8. The method of claim 1, further comprising repeating steps (a), (b), and (c) a plurality of times.

9. The method of claim 1, wherein steps (b) and (c) are performed simultaneously.

10. The method of claim 1, wherein steps (b) and (c) are performed sequentially.

11. The method of claim 1, wherein the vessel comprises a volume of at least 100 liters.

12. The method of claim 1, wherein the growth media in steps (a) and (c) is sterilized.

13. The method of claim 1, wherein step (a) uses an air lift or bubble column reactor.

14. The method of claim 1, wherein step (a) uses an agitator.

15. The method of claim 1, wherein the doubling rate of *Euglena* in step (a) is between 10 and 30 hours.

16. The method of claim 1, wherein the growth media in steps (a) and (c) comprises ammonium hydroxide as the primary nitrogen source.

17. The method of claim 1, wherein the growth media in steps (a) and (c) comprises a citrate-citric acid buffer.

18. The method of claim 1, wherein the growth media in steps (a) and (c) comprises ethanol as a carbon source.

19. The method of claim 1, wherein the removed portion of step (b) comprises less than 2 grams of a carbon source for every 1 gram of *Euglena*.

20. The method of claim 1, further comprising separating the removed portion of step (b) into a solid portion comprising the *Euglena* and a liquid portion.

21. The method of claim 20, further comprising drying the solid portion to form an algae biomass.

22. The method of claim 21, further comprising reducing the average particle size of the algae biomass to 1000 microns or less.

23. The method of claim 21, further comprising reducing the average particle size of the algae biomass to 500 microns or less.

24. The method of claim 1, further comprising extracting the removed portion of step (b) to isolate paramylon from the *Euglena*.

25. The method of claim 1, wherein the vessel is a bioreactor.

26. The method of claim 1, wherein the volume of fresh growth media in step (c) is equal to the volume of the removed portion in step (b).

27. The method of claim 1, wherein the vessel comprises a volume of at least 5000 liters.

28. The method of claim 1, wherein step (a) does not use an agitator blade.

29. The method of claim 1, wherein steps (a), (b), and (c) are repeated for up to 25 days.

* * * * *